(12) United States Patent
Chappell et al.

(10) Patent No.: US 8,704,040 B2
(45) Date of Patent: Apr. 22, 2014

(54) ***B. BRAUNII*, RACE B GENE FOR A TRITERPENE METHYLTRANSFERASE ENZYME AND USES THEREOF**

(75) Inventors: Joseph Chappell, Lexington, KY (US); Shigeru Okada, Tokyo (JP); Scott Kinison, Lexington, KY (US); Tom Niehaus, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 1027 days.

(21) Appl. No.: 12/489,038

(22) Filed: Jun. 22, 2009

(65) Prior Publication Data

US 2010/0009423 A1 Jan. 14, 2010

Related U.S. Application Data

(60) Provisional application No. 61/074,351, filed on Jun. 20, 2008.

(51) Int. Cl.
*C12N 15/29* (2006.01)
*C12N 15/52* (2006.01)
*C12N 15/82* (2006.01)

(52) U.S. Cl.
USPC ........... 800/287; 800/296; 800/297; 800/298; 536/23.6; 435/254.11; 435/320.1; 435/325; 435/419

(58) Field of Classification Search
None
See application file for complete search history.

(56) References Cited

PUBLICATIONS

Niehaus, T. et al. Journal of Biological Chemistry; published online Jan. 12, 2012.*
GenBank Accession GI: 158279461 (Nov. 7, 2007) sterol-C24-methyltransferase [*Chlamydomonas reinhardtii*].*

* cited by examiner

*Primary Examiner* — Russell Kallis
(74) *Attorney, Agent, or Firm* — Crowell & Moring LLP

(57) ABSTRACT

Provided is an isolated polypeptide having triterpene methyltransferase activity. Also provided is an isolated nucleic acid molecule that encodes the triterpene methyltransferase polypeptides; a vector comprising the nucleic acid molecules that encode the triterpene methyltransferase polypeptides; and a host cell(s) transfected with the aforementioned nucleic acid molecule or vector. In another aspect, a method of producing a methylated triterpene is provided. The method comprises providing a metabolizable carbon source to a host cell transfected with a nucleic acid molecule that encodes a triterpene methyltransferase under conditions sufficient for production of a methylated triterpene. The method optionally further comprises isolating the methylated triterpene produced by the host cell.

22 Claims, 13 Drawing Sheets

ATGGCCCTGGATCTTCTTTCATCCTACGCTCCTGGCTTGGTCGAAAGCCTGCTAACATGGAA
AGGCGCAGCCGGCTTGGCTGCAGCTGTTGCCCTGGGCTATATTATTATAAGCAACCTTCCTG
GAAGGCAGGTTGCTAAGCCCAGCCTTCTTCAAGTCAGAACTGGTGGCGTCGCCTTCGAGAAG
GTCGCTGAGGTAGTTGCCGACTACAGTGACTCTTACGGGCAAACTGAAAAGGGCGAACTCAT
CGTCAAGGACAACAACAAGATTGTCTCTCTCGCGAATACTTTCTATGACCTCATCACCGATG
GATATGAGTGGGGATGGGGCTCCGGCTTCCACTTCTCTCATAGGCTGCCAGGGATGTCCTTC
AATGCATCTCAGCTGCTCCATGAGTCCCGTATGGCGTCTTTCCTGCGCCTGAAGCCCGGCAT
GCAAGTTCTTGATGTTGGCTGCGGTGTCGGAAACCCTGGCAGAACGGTTGCTGCCTGCAGTG
GAGCAGTGGTGACTGGCATCACCATCAATGCATACCAGATCAAGCGCGCTGAGTTGCACACT
AAGCGGGCGGGCTTGGTAGGATACTTCAAGCCAGTTCAGGGAAACTTCTGCGCGATGCCTTT
CCAAGACAAGAGCTTCGATGCTGCCTTTGCCATGGACTCTACTTGCCATGCCCCCAAGCTGG
AGGATGTGTACTCCGAGGTCTTCCGCGTGTTGAAGCCTGGCGCATACTTTGCAACTTATGAG
TGGGTGTCTACAAAGAACTACGACTCCAACAACCCAGAGCACGTGAAGTGCATGAACAGCAT
CATCCTGGGCAATGGCCTGCCGAACATCAGGAGTTGGAAGCAAGCTGAGGAGGCAGGGAAGA
ACGTGGGTTTCAACCTGCTTACCAGCCTCGACATGGCTACAAACTCCCCCATCGGAAAGCCC
TGGTACTCTGTCCCAGAGCGCATGGTAAACTGGGGCCTGTTCCGTTTCCACAAGGCTTGCAT
TCGCACTGCCTCTACCCTGCATCTGCTGCCGCCAGAATCCTGGAAGTTCTTCTACATCCTTG
CAGAGATGGCCGAGAACCTTGTAAAGGGTGGGCAATGGGACATCTTCACCCCCATGCACTTG
CTGATCTTCCAAAAGCCAGAGTAA

FIG. 1

MALDLLSSYAPGLVESLLTWKGAAGLAAAVALGYIIISNLPGRQVAKPSLLQVRTGGVAFEK
VAEVVADYSDSYGQTEKGELIVKDNNKIVSLANTFYDLITDGYEWGWGSGFHFSHRLPGMSF
NASQLLHESRMASFLRLKPGMQVLDVGCGVGNPGRTVAACSGAVVTGITINAYQIKRAELHT
KRAGLVGYFKPVQGNFCAMPFQLKSFDAAFAMDSTCHAPKLEDVYSEVFRVLKPGAYFATYE
WVSTKNYDSNNPEHVKCMNSIILGNGLPNIRSWKQAEEAGKNVGFNLLTSLDMATNSPIGKP
WYSVPERMVNWGLFRFHKACIRTASTLHLLPPESWKFFYILAEMAENLVKGGQWDIFTPMHL
LIFQKPE

FIG. 2

| Peak # | Compound | (mg/L) |
|---|---|---|
| 1 | Squalene | 121.58 |
| 2 | Methylsqualene | 2.08 |
| 3 | Dimethylsqualene | 0.46 |
| 4 | Trimethylsqualene | 0.35 |

B. BRAUNII, RACE B GENE FOR A TRITERPENE METHYLTRANSFERASE ENZYME AND USES THEREOF

FIELD OF THE INVENTION

The invention relates to triterpene methyltransferase and its use in producing methylated triterpenes.

BACKGROUND OF THE INVENTION

Squalene and botryococcene are related by their putative biosynthetic origins from the condensation of two farnesyl diphosphate (FPP) molecules, a common biosynthetic intermediate found in the mevalonate biosynthetic pathway, and are known to be synthesized by *Botryococcus braunii*, race B, a fresh water algae (Okada et al., *J. Appl. Phycology,* 7: 555-559, 1995; Metzger et al., *Appl. Microbiol. Biotech.,* 66: 486-496, 2005). *Botryococcus braunii* is known for its ability to accumulate large amounts of hydrocarbons. In particular *B. braunii* race B can accumulate 20-50% its dry weight of C30-C34 botryococcenes and squalenes.

Squalene, botryococcene and their methylated derivatives from *B. braunii* have attracted significant attention because these molecules are thought to be the progenitors to current oil shale deposits (Summons et al., Organic Geochem., 33: 99-109, 2002; Walters et al., AAPG Bulletin, 89: 1239-1244, 2005) and because they are considered promising renewable, alternative biofuels (Banerjee et al., *Crit. Rev. Biotech.,* 22: 245-279 (2002)). For example, Hillen et al. (Biotech. Bioeng., 24: 193-205, 1982) previously reported on the catalytic cracking of oils extracted from *Botryococcus braunii*, primarily the methylated botryococcenes and squalene derivatives, and observed an overall conversion of 79% of the oil to combustible fuels under standard cracking conditions. Overall, 67% of the converted oil was to gasoline grade fuel (octanes), 15% to aviation turbine fuel, and 15% to diesel fuel with a residual of only 3%. Hence, catalytic hydrolysis (as performed in standard petroleum refineries) of these highly branched, poly-unsaturated triterpenes results in the generation of hydrocarbon fractions that are chemically equivalent to those derived from current petroleum deposits and are of direct utility as fuels for internal combustion engines, as well as feedstocks for chemical manufacturing (Banerjee et al., 2002).

These energy-rich triterpene oils have only been available from cultures of *Botryococcus braunii*, a rather slow growing green algae that does not lend itself to large-scale or fermentation type culturing conditions (Casadevall et al., *Biotech. Bioeng.,* 27: 286-295 (1985)). Thus, there is a need for improved sources of these energy-rich triterpene oils.

SUMMARY OF THE INVENTION

In one aspect, the present invention relates to an isolated polypeptide which is a triterpene methyltransferase, for example a *Botryococcus braunii* triterpene methyltransferase comprising the amino acid sequence of SEQ ID NO:2 as well as variants, conservative variants, and fragments thereof.

Another aspect of the present invention relates to an isolated nucleic acid molecule that encodes a polypeptide of this invention, e.g., isolated nucleic acid molecule encoding SEQ ID NO: 2 and conservative variants and fragments thereof including, e.g., SEQ ID NO: 1.

In another aspect, the present invention provides a vector comprising a nucleic acid molecule(s) of this invention that encodes a triterpene methyltransferase polypeptide of this invention. In yet another aspect, the present invention provides a host cell transfected with the aforementioned nucleic acid molecule or vector.

In another aspect, the present invention provides a method of producing a methylated triterpene of this invention. The method comprises providing a metabolizable carbon source to a host cell transfected with a nucleic acid molecule of this invention that encodes a triterpene methyltransferase under conditions sufficient for production of a methylated triterpene. The method optionally further comprises isolating the methylated triterpene produced by the host cell.

Other methods, features and advantages of the present invention will be or become apparent to one with skill in the art upon examination of the following detailed descriptions. It is intended that all such additional methods, features and advantages be included within this description, be within the scope of the present invention, and be protected by the accompanying claims.

BRIEF DESCRIPTION OF THE DRAWINGS

FIG. 1 shows the DNA sequence for the *B. braunii* triterpene methyltransferase cDNA SEQ ID NO: 1. The start and stop codons are shown in bold.

FIG. 2 shows the predicted amino acid sequence for the *B. braunii* triterpene methyltransferase protein, SEQ ID NO: 2.

DETAILED DESCRIPTION OF THE INVENTION

Figure 3:
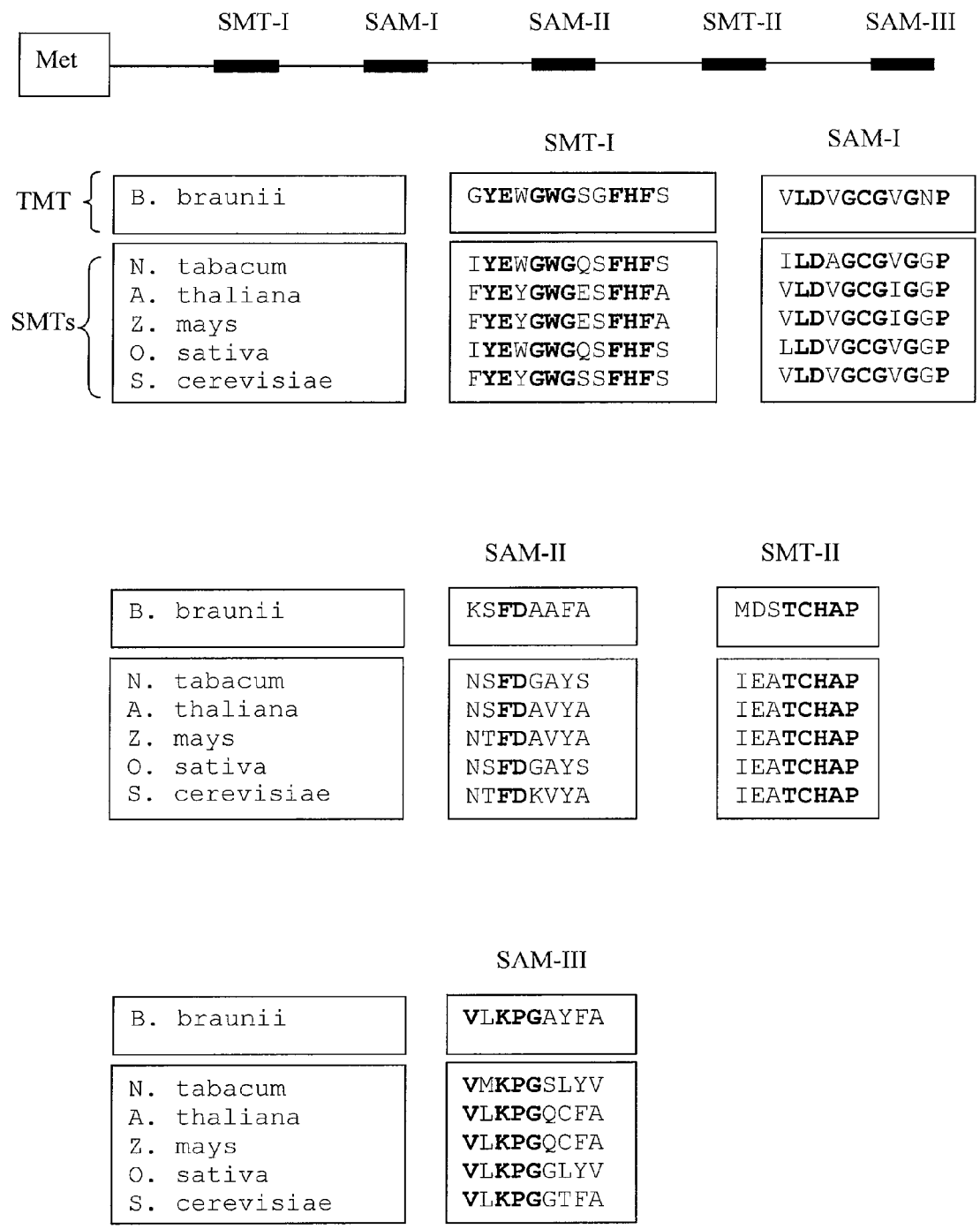
FIG. 3 illustrates a comparison of putative SAM (S-adenosyl methionine) and SMT (sterol methyltransferase specific) binding motifs in sterol methyltransferase genes from a variety of plants and *Botryococcus braunii* triterpene methyltransferase. Peptide domain sequences 5'-3' for: *B. braunii* SEQ ID NO: 14, 15, 16, 17 and 18; *N. tabacum* SEQ ID NO: 19, 20, 21, 22 and 23; *A. thalina* SEQ ID NO: 24, 25, 26, 27; and 28 *Z. mays* SEQ ID NO: 29, 30, 31, 32; and 33 *Osativa* SEQ ID NO: 34, 35, 36, 37 and 38; *S. cerevisiae* SEQ ID NO: 39, 40, 41, 42 and 43.

Before the present compositions and methods are described, it is to be understood that the invention is not limited to the particular methodologies, protocols, assays, and reagents described, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless the context clearly dictates otherwise.

Unless defined otherwise, all technical and scientific terms used herein have the same meanings as commonly understood by one of ordinary skill in the art to which this invention belongs. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The present inventors have discovered an improved source of energy-rich triterpene oils. Among other things, the present inventors provide elucidation of the structural and functional characteristics of a triterpene methyltransferase gene from *Botryococcus braunii*. The *B. braunii* triterpene methyltransferase can be used to produce methylated linear triterpene hydrocarbons such as methylated botryococcenes and methylated squalenes.

These methylated botryococcenes and squalenes can be easily converted into high octane fuel for use in combustion engines. Because of this, *B. braunii* has attracted much interest as a potential renewable fuel source. However, due to its slow growing nature and aquatic habitat, cultivation of *B. braunii* for hydrocarbon production remains technically and economically difficult. The compositions and methods described herein provide a mechanism to overcome these difficulties.

Described herein are the nucleotide and amino acid sequences and functional characterization of a triterpene methyltransferase gene which, when expressed in a heterologous host such as a bacteria, yeast or plant, provides an enzyme activity that catalyzes the successive methylation of linear triterpene hydrocarbons such as squalene and botryococcene, generating branched-chain hydrocarbons. The encoded methyltransferase activity can methylate squalene, for example, 1 to 4 times, generating mono-, di-, tri- and tetra-methylated squalenes derivatives. Botryococcene can likewise be methylated to form, for example, mono-, di-, tri- and tetra-methylated botryococcenes.

The identification of the triterpene methyltransferase nucleic acid molecule and its encoded polypeptide, e.g. a polypeptide comprising the sequence set forth in SEQ ID NO: 2 or a variant or fragment thereof having triterpene methyltransferase activity, provides a means of generating important raw materials for the reliable and cost effective production of an energy-rich, renewable, and sustainable biofuel source. For example, the co-expression of the triterpene methyltransferase in combination with suitable farnesyl diphosphate (FPP) synthase and triterpene synthase in transgenic terrestrial plants could yield a production platform for methylated triterpenes. These compounds would be derived from the metabolic diversion of $CO_2$ fixed in the process of photosynthesis flowing directly into triterpene biosynthesis and accumulation.

Thus, in one aspect the present invention provides a nucleic acid molecule encoding a triterpene methyltransferase. In another aspect, the present invention provides a polypeptide encoded by a triterpene methyltransferase nucleic acid molecule. A triterpene methyltransferase polypeptide can methylate a triterpene, e.g., squalene or botryococcene, to generate a mono-, di-, tri- or tetra-methylated triterpene. A triterpene methyltransferase from any species may be used, including an algal triterpene methyltransferase, such as a *Botryococcus braunii* triterpene methyltransferase. For example, FIG. 1 shows the DNA sequence encoding a *B. braunii* triterpene methyltransferase of this invention (SEQ ID NO:1), and FIG. 2 shows the amino acid sequence of a *B. braunii* triterpene methyltransferase of this invention (SEQ ID NO:2). It should be understood that the invention is not limited to use of triterpene methyltransferase sequences of SEQ ID NO:1 or SEQ ID NO:2. That is, any naturally-occurring triterpene methyltransferase may be used, whether derived from *B. braunii* or any other algal or other organism. In addition to naturally-occurring triterpene methyltransferase, synthetic variants of SEQ ID NO:1 or SEQ ID NO:2 may be employed.

While these variants will be described in more detail below, it is understood that polypeptides of the invention may contain one or more modified amino acids. The presence of modified amino acids may be advantageous in, for example, increasing triterpene methyltransferase catalytic activity or increasing polypeptide stability. Amino acid(s) are modified, for example, co-translationally or post-translationally during recombinant production (e.g., N-linked glycosylation at N—X—S/T motifs during expression in mammalian cells) or modified by synthetic means. Accordingly, a "mutant", "variant" or "modified" protein, enzyme, polynucleotide, gene, or cell, means a protein, enzyme, polynucleotide, gene, or cell, that has been altered or derived, or is in some way different or changed, from a parent protein, enzyme, polynucleotide, gene, or cell. A mutant or modified protein or enzyme is usually, although not necessarily, expressed from a mutant polynucleotide or gene.

A "parent" protein, enzyme, polynucleotide, gene, or cell, is any protein, enzyme, polynucleotide, gene, or cell, from which any other protein, enzyme, polynucleotide, gene, or cell, is derived or made, using any methods, tools or techniques, and whether or not the parent is itself native or mutant. A parent polynucleotide or gene encodes for a parent protein or enzyme.

A "mutation" means any process or mechanism resulting in a mutant protein, enzyme, polynucleotide, gene, or cell. This includes any mutation in which a protein, enzyme, polynucleotide, or gene sequence is altered, and any detectable change in a cell arising from such a mutation. Typically, a mutation occurs in a polynucleotide or gene sequence, by point mutations, deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent", i.e., not reflected in an amino acid alteration upon expression, leading to a "sequence-conservative" variant of the gene. This generally arises when one amino acid corresponds to more than one codon.

Non-limiting examples of a modified amino acid include a glycosylated amino acid, a sulfated amino acid, a prenlyated (e.g., farnesylated, geranylgeranylated) amino acid, an acetylated amino acid, an acylated amino acid, a pegylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols on CD-ROM (Humana Press, Towata, N.J.).

Recombinant methods for producing and isolating modified triterpene methyltransferase polypeptides of the invention are described herein. In addition to recombinant production, the polypeptides may be produced by direct peptide synthesis using solid-phase techniques (e.g., Stewart et al. (1969) Solid-Phase Peptide Synthesis (WH Freeman Co, San Francisco); and Merrifield (1963) *J. Am. Chem. Soc.* 85: 2149-2154; each of which is incorporated by reference). Peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer.

A "protein" or "polypeptide", which terms are used interchangeably herein, comprises one or more chains of chemical building blocks called amino acids that are linked together by chemical bonds called peptide bonds. An "enzyme" means any substance, composed wholly or largely of protein, that catalyzes or promotes, more or less specifically, one or more chemical or biochemical reactions. The term "enzyme" can also refer to a catalytic polynucleotide (e.g., RNA or DNA). A "native" or "wild-type" protein, enzyme, polynucleotide, gene, or cell, means a protein, enzyme, polynucleotide, gene, or cell that occurs in nature.

Accordingly, this invention also provides in various embodiments, isolated or recombinant polypeptides comprising the amino acid sequence set forth in SEQ ID NO:2, an amino acid sequence that is at least 20%, 30%, 33%, 35%, 37%, 40%, 44%, 50%, 53%, 60%, 70%, 80%, 90%, 95% and 99% identical to the full-length amino acid sequence of SEQ ID NO:2, and polypeptides comprising SEQ ID NO: 2 except that up to e.g., 35, 25, 10, 5, 4, 3, 2 or 1 of the amino acids of SEQ ID NO:2 are conservative amino acid substitutions. Preferably the polypeptides have triterpene methyltransferase activity, e.g. approximately the level of triterpene methyltransferase activity of a polypeptide of SEQ ID NO: 2, or higher than such level.

"Conservative amino acid substitutions" of a particular sequence refers to the replacement of one amino acid, or series of amino acids, with essentially identical amino acid or series of amino acids. One of skill will recognize that individual substitutions, deletions or additions which alter, add or delete a single amino acid or a percentage of amino acids in an encoded sequence result in "conservative variations" where the alterations result in the deletion of an amino acid, addition of an amino acid, or substitution of an amino acid with a functionally similar amino acid.

Conservative substitution tables providing functionally similar amino acids are well known in the art. For example, one conservative substitution group includes Alanine (A), Serine (S), and Threonine (T). Another conservative substitution group includes Aspartic acid (D) and Glutamic acid (E). Another conservative substitution group includes Asparagine (N) and Glutamine (Q). Yet another conservative substitution group includes Arginine (R) and Lysine (K). Another conservative substitution group includes Isoleucine, (I) Leucine (L), Methionine (M), and Valine (V). Another conservative substitution group includes Phenylalanine (F), Tyrosine (Y), and Tryptophan (W).

Thus, "conservative amino acid substitutions" of a listed polypeptide sequence (e.g., SEQ ID NO:2) include substitutions of a percentage, typically less than 15% or less than 10%, of the amino acids of the polypeptide sequence, with an amino acid of the same conservative substitution group. Accordingly, a conservatively substituted variation of a polypeptide of the invention can contain, for example, substitutions of e.g., 40, 35, 25, 10, 5, 4, 3, 2 or 1 amino acid with an amino acid of the same conservative substitution group.

It is understood that the addition of sequences that do not alter the encoded activity of a nucleic acid molecule, such as the addition of a non-functional or non-coding sequence, is a conservative variation of the basic nucleic acid molecule. The "activity" of an enzyme is a measure of its ability to catalyze a reaction, i.e., to "function", and may be expressed as the rate at which the product of the reaction is produced. For example, enzyme activity can be represented as the amount of product produced per unit of time or per unit of enzyme (e.g., concentration or weight), or in terms of affinity or dissociation constants. As used interchangeably herein a "triterpene methyltransferase activity", "biological activity of triterpene methyltransferase" or "functional activity of triterpene methyltransferase", refers to an activity exerted by a triterpene methyltransferase protein, polypeptide or nucleic acid molecule on a triterpene methyltransferase polypeptide substrate, as determined in vivo, or in vitro, according to standard techniques.

One of skill in the art will appreciate that many conservative variations of the nucleic acid constructs which are disclosed herein yield a functionally identical construct. For example, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the polypeptides provided herein.

It will be appreciated by those skilled in the art that due to the degeneracy of the genetic code, a multitude of nucleotide sequences encoding modified triterpene methyltransferase polypeptides of the invention may be produced, some of which bear substantial identity to the nucleic acid sequences explicitly disclosed herein. For instance, codons AGA, AGG, CGA, CGC, CGG, and CGU all encode the amino acid arginine. Thus, at every position in the nucleic acid molecules of the invention where an arginine is specified by a codon, the codon can be altered to any of the corresponding codons described above without altering the encoded polypeptide. It is understood that U in an RNA sequence corresponds to T in a DNA sequence.

"Conservative variants" are proteins or enzymes in which a given amino acid residue has been changed without altering overall conformation and function of the protein or enzyme, including, but not limited to, replacement of an amino acid with one having similar properties, including polar or nonpolar character, size, shape and charge. Amino acids other than those indicated as conserved may differ in a protein or enzyme so that the percent protein or amino acid sequence similarity between any two proteins of similar function may vary and can be, for example, at least 30%, at least 32%, at least 37%, at least 44%, at least 50%, at least 53%, at least 70%, at least 80%, at least 90%, at least 95%, at least 98% or at least 99%, as determined according to an alignment scheme. As referred to herein, "sequence similarity" means the extent to which nucleotide or protein sequences are related. The extent of similarity between two sequences can be based on percent sequence identity and/or conservation. "Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, 1985 Science 22; 227(4693):1435-41; Pearson and Lipman, 1988 Proc Natl Acad Sci USA, 85(8):2444-8). When using all of these programs, the preferred settings are those that results in the highest sequence similarity.

Non-conservative modifications of a particular polypeptide are those which substitute any amino acid not characterized as a conservative substitution. For example, any substitution which crosses the bounds of the six groups set forth above. These include substitutions of basic or acidic amino acids for neutral amino acids, (e.g., Asp, Glu, Asn, or Gln for Val, Ile, Leu or Met), aromatic amino acid for basic or acidic amino acids (e.g., Phe, Tyr or Trp for Asp, Asn, Glu or Gln) or any other substitution not replacing an amino acid with a like amino acid. Basic amino acids include lysine (K), arginine (R), histidine (H); acidic amino acids include aspartic acid (D), glutamic acid (E); uncharged polar amino acids include glycine (G), asparagine (N), glutamine (Q), serine (S), threonine (T), tyrosine (Y), cysteine (C); nonpolar amino acids include alanine (A), valine (V), leucine (L), isoleucine (I), proline (P), phenylalanine (F), methionine (M), tryptophan (W); beta-branched amino acids include threonine (T), valine (V), isoleucine (I); aromatic amino acids include tyrosine (Y), phenylalanine (F), tryptophan (W), histidine (H).

A polynucleotide, polypeptide, or other component is "isolated" when it is partially or completely separated from components with which it is normally associated (other proteins, nucleic acid molecules, cells, synthetic reagents, etc.). A nucleic acid molecule or polypeptide is "recombinant" when it is artificial or engineered, or derived from an artificial or engineered protein or nucleic acid molecule. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant. For example, an "isolated" nucleic acid molecule is one which is separated from other nucleic acid molecules which are present in the natural source of the nucleic acid molecule. For example, with regards to genomic DNA, the term "isolated" includes nucleic acid molecules which are separated from the chromosome with which the genomic DNA is naturally associated. Typically, an "isolated" nucleic acid molecule is free of sequences which naturally flank the nucleic acid molecule (i.e., sequences located at the 5' and 3' ends of the nucleic acid molecule) in the genomic DNA of the organism from which the nucleic acid molecule is derived. For example, in various embodiments, the isolated nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid molecule is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

In some embodiments, a polypeptide provided herein includes amino acid residue substitutions that correspond to positions in a particular sequence at least 80%, 85%, 90%, 95, 98 or 99% of the time. In other words, the invention encompasses polypeptides that contain the recited amino acid substitutions at 80%, 85%, 90%, 95, 98 or 99% of the recited positions in a given sequence. The skilled artisan will recognize that not every substitution from a group of substitutions is necessary to obtain a modified polypeptide that is active on a triterpene substrate.

"Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, 1985; Pearson and Lipman, 1988). When using all of these programs, the preferred settings are those that results in the highest sequence similarity. For example, the "identity" or "percent identity" with respect to a particular pair of aligned amino acid sequences can refer to the percent amino acid sequence identity that is obtained by ClustalW analysis (version W 1.8 available from European Bioinformatics Institute, Cambridge, UK, counting the number of identical matches in the alignment and dividing such number of identical matches by the greater of (i) the length of the aligned sequences, and (ii) 96, and using the following default ClustalW parameters to achieve slow/accurate pairwise alignments—Gap Open Penalty: 10; Gap Extension Penalty: 0.10; Protein weight matrix: Gonnet series; DNA weight matrix: IUB; Toggle Slow/Fast pairwise alignments=SLOW or FULL Alignment. See also Larkin M A, Blackshields G, Brown N P, Chema R, McGettigan P A, McWilliam H, Valentin F, Wallace I M, Wilm A, Lopez R, Thompson J D, Gibson T J, Higgins D G. (2007). Clustal W and Clustal X version 2.0. *Bioinformatics,* 23, 2947-2948.)

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art and described, e.g., in Dayhoff (1978) "A model of evolutionary change in proteins" in "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) *Proc. Natl. Acad. Sci. USA* 89: 10915-10919 (each of which is incorporated in its entirety by reference). The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm, e.g., gapped BLAST 2.0, described in Altschul et al. (1997) *Nucl. Acids Res.* 25: 3389-3402 (incorporated by reference herein), and made available to the public at the National Center for Biotechnology Information (NCBI) Website (www.ncbi.nlm.nih.gov). Optimal alignments, including multiple alignments, can be prepared using, e.g., PSI-BLAST, available through the NCB1 website and described by Altschul et al. (1997) *Nucl. Acids Res.* 25:3389-3402 (incorporated by reference herein).

With respect to an amino acid sequence that is optimally aligned with a reference sequence, an amino acid residue "corresponds to" the position in the reference sequence with which the residue is paired in the alignment. The "position" is denoted by a number that sequentially identifies each amino acid in the reference sequence based on its position relative to the N-terminus. For example, in SEQ ID NO:2 as the reference sequence, position 1 is M, position 2 is A, position 3 is L, etc. When a test sequence is optimally aligned with SEQ ID NO:2, a residue in the test sequence that aligns with the L at position 3 is said to "correspond to position 3" of SEQ ID NO:2. Owing to deletions, insertion, truncations, fusions, etc., that must be taken into account when determining an optimal alignment, in general the amino acid residue number in a test sequence as determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

Also contemplated are fragments of the full length triterpene methyltransferase polypeptides and polynucleotides, e.g., fragments of polypeptides, wherein the polypeptide comprises the amino acid sequence set forth in SEQ ID NO: 2 and fragments of nucleic acid molecules, wherein the nucleic acid molecules comprises the sequence set forth in SEQ ID NO: 1. For example a fragment of this invention is a fragment of SEQ ID NO: 2 or SEQ ID NO: 1 comprising the SMT-II domain, SEQ ID NO:17, or encoding the SMT-II domain. A "fragment" is a unique portion of a triterpene methyltransferase polypeptide or the polynucleotide encoding triterpene methyltransferase which is identical in sequence to, but shorter in length than, the parent sequence. A fragment may comprise up to the entire length of the defined sequence, minus one nucleotide/amino acid residue. For example, a fragment may comprise from 5 to 1000 contiguous nucleotides or amino acid residues of a given nucleic acid molecule or polypeptide. A fragment used as a probe, primer, antigen, catalytic molecule, or for other purposes, may be at least 5, 10, 15, 16, 20, 25, 30, 40, 50, 60, 75, 100, 150, 250 or at least 500 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25% or 50%) of a polypeptide as shown in a certain defined sequence. Clearly these lengths are exemplary, and any length that is supported by the specification, including the Sequence Listing, tables, and figures, may be encompassed by the present embodiments.

Also contemplated in this invention are isolated polypeptides that are methyltransferases, preferably triterpene methyltransferases, that comprise 5 peptide domains, each peptide domain comprising at least 9 amino acids, wherein three of the domains, SAM-I, SAM-II and SAM-III, are associated with binding of a common methyl donor (SAM binding domains), and two peptide domains, SMT-I and SMT-II, are associated with catalytic transfer of methyl substituents from a methyl donor to a methyl acceptor. The SMT-I, SAM-I, SAM-II, SMT-II and SAM-III domains of the triterpene methyltransferases of this invention may comprise respectively, e.g., SEQ ID NO: 14, SEQ ID NO: 15, SEQ ID NO: 16, SEQ ID NO: 17 and SEQ ID NO: 18 (See FIG. 3, the 5 domains of *B. braunii*). In an embodiment of the invention, the SMT-I domain comprises an amino acid sequence that is at least 20%, 30%, 40%, 50%, 60%, 62%, 70%, 77%, 80%, 90% or 95% identical to the full-length of SEQ ID NO: 14, the SAM-I domain comprises an amino acid sequence that is at least 20%, 30%, 38%, 40%, 50%, 60%, 63%, 70%, 78%, 80%, 89%, 90% or 95% identical the full-length of SEQ ID NO: 15, the SAM-II peptide domain may comprises an amino acid sequence that is at least 20%, 30%, 40%, 50%, 60%, 63%, 70%, 80%, 90% or 95% identical to the full-length of SEQ ID NO: 16, the SMT-II peptide domain comprises an amino acid sequence that is at least 20%, 30%, 40%, 50%, 60%, 70%, 80%, 90% or 95% identical to the full-length of SEQ ID NO: 17 and the SAM-III peptide domain comprises an amino acid sequence that is at least 20%, 30%, 40%, 50%, 60%, 70%, 80%, 90% or 95% identical the full-length of SEQ ID NO: 18. The SMT-II peptide domain may also comprise an amino acid sequence that is at least 20%, 30%, 40%, 50%, 60%, 63%, 70%, 80%, 90% or 95% identical to the full-length of SEQ ID NO: 16, with the proviso that the sequence does not comprise amino acid sequence IEATCHAP (SEQ ID NO: 22). The 5 peptide domains may be present in the methyltransferase in any order, preferably the order of the 5 peptides in the polypeptide is, from its amino to carboxy terminal, SMT-I, SAM-I, SAM-II, SMT-II and SAM-III, and more preferably the SMT-I, SAM-I, SAM-II, SMT-II and SAM-III peptide domains comprise respectively the *B. braunii* sequences in FIG. 3, SEQ ID NO: 14, SEQ ID NO: 15, SEQ ID NO: 16, SEQ ID NO: 17 and SEQ ID NO: 18.

In other embodiments, isolated nucleic acid molecules are provided. In one aspect, the invention provides a novel family of isolated or recombinant polynucleotides referred to herein as "triterpene methyltransferase polynucleotides" or "triterpene methyltransferase nucleic acid molecules." Triterpene methyltransferase polynucleotide sequences are characterized by the ability to encode a triterpene methyltransferase polypeptide. In general, the invention includes any nucleotide sequence that encodes any of the novel triterpene methyltransferase polypeptides described herein. The invention provides nucleic acid molecules encoding a triterpene methyltransferase having the sequence set forth in SEQ ID NO: 2 or conservative variants thereof. In particular the invention provides nucleic acid molecules comprising SEQ ID NO: 1. The invention also provides isolated or recombinant polynucleotides that encode the polypeptide domains described herein. The terms "polynucleotide," "nucleotide sequence," and "nucleic acid molecule" are used to refer to a polymer of nucleotides (A, C, T, U, G, etc. or naturally occurring or artificial nucleotide analogues), e.g., DNA or RNA, or a representation thereof, e.g., a character string, etc., depending on the relevant context. A given polynucleotide or polynucleotide complementary to the entire length of a given polynucleotide can be determined from any specified nucleotide sequence.

In one aspect, the triterpene methyltransferase polynucleotides comprise recombinant or isolated forms of naturally occurring nucleic acid molecules isolated from an organism, e.g., an algae strain. Exemplary triterpene methyltransferase polynucleotides include those that encode the wild-type polypeptide set forth in SEQ ID NO:2. In another aspect of the invention, triterpene methyltransferase polynucleotides are produced by diversifying, e.g., mutating a naturally occurring, isolated, or recombinant triterpene methyltransferase polynucleotide. It is possible to generate diversified triterpene methyltransferase polynucleotides encoding triterpene methyltransferase polypeptides with superior functional attributes, e.g., increased catalytic function, increased stability, or higher expression level, than a triterpene methyltransferase polynucleotide used as a substrate or parent in the diversification process.

The polynucleotides of the invention have a variety of uses in, for example recombinant production (i.e., expression) of the triterpene methyltransferase polypeptides of the invention and as substrates for further diversity generation, e.g., recombination reactions or mutation reactions to produce new and/or improved triterpene methyltransferase homologues, and the like.

It is important to note that certain specific, substantial and credible utilities of triterpene methyltransferase polynucleotides do not require that the polynucleotide encode a polypeptide with substantial triterpene methyltransferase activity or even variant triterpene methyltransferase activity. For example, triterpene methyltransferase polynucleotides that do not encode active enzymes can be valuable sources of parental polynucleotides for use in diversification procedures to arrive at triterpene methyltransferase polynucleotide variants, or non-triterpene methyltransferase polynucleotides, with desirable functional properties (e.g., high kcat or kcat/Km, low Km, high stability towards heat or other environmental factors, high transcription or translation rates, resistance to proteolytic cleavage, etc.).

Triterpene methyltransferase polynucleotides of this invention, including nucleotide sequences that encode triterpene methyltransferase polypeptides and variants thereof, fragments of triterpene methyltransferase polypeptides, related fusion proteins, or functional equivalents thereof, are used in recombinant DNA molecules that direct the expression of the triterpene methyltransferase polypeptides in appropriate host cells, such as plant cells. Due to the inherent degeneracy of the genetic code, other nucleic acid sequences which encode substantially the same or a functionally equivalent amino acid sequence can also be used to clone and express the triterpene methyltransferase polynucleotides. The term "host cell", as used herein, includes any cell type which is susceptible to transformation with a nucleic acid construct. The term "transformation" means the introduction of a foreign (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may include regulatory or control sequences, such as start, stop, promoter, signal, secretion, or other sequences used by the genetic machinery of the cell. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

As will be understood by those of skill in the art, it can be advantageous to modify a coding sequence to enhance its expression in a particular host. The genetic code is redundant with 64 possible codons, but most organisms preferentially use a subset of these codons. The codons that are utilized most often in a species are called optimal codons, and those not utilized very often are classified as rare or low-usage codons (see, e.g., Zhang et al. (1991) *Gene* 105:61-72; incorporated by reference herein). Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) *Nucl. Acids Res.* 17:477-508; incorporated by reference herein) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, preferred stop codons for *S. cerevisiae* and mammals are UAA and UGA, respectively. The preferred stop codon for monocotyledonous plants is UGA, whereas insects and *E. coli* prefer to use UAA as the stop codon (Dalphin et al. (1996) *Nucl. Acids Res.* 24: 216-218; incorporated by reference herein). Methodology for optimizing a nucleotide sequence for expression in a plant is provided, for example, in U.S. Pat. No. 6,015,891, and the references cited therein, (incorporated herein by reference).

"Silent variations" are one species of "conservative variations." One of skill will recognize that each codon in a nucleic acid sequence (except AUG, which is ordinarily the only codon for methionine) can be modified by standard techniques to encode a functionally identical polypeptide. Accordingly, each silent variation of a nucleic acid sequence that encodes a polypeptide is implicit in any described sequence. The invention provides each and every possible variation of nucleic acid sequence encoding a polypeptide of the invention that could be made by selecting combinations based on possible codon choices. These combinations are made in accordance with the standard triplet genetic code as applied to the nucleic acid sequence encoding a triterpene methyltransferase homologue polypeptide of the invention. All such variations of every nucleic acid sequence herein are specifically provided and described by consideration of the sequence in combination with the genetic code. Any variant can be produced as noted herein.

In general, the invention includes any polypeptide encoded by a modified triterpene methyltransferase polynucleotide derived by mutation, recursive sequence recombination, and/or diversification of the polynucleotide sequences described herein. In some aspects of the invention, a triterpene methyltransferase polypeptide is modified by single or multiple amino acid substitutions, a deletion, an insertion, or a combination of one or more of these types of modifications. Substitutions can be conservative or non-conservative, can alter function or not, and can add new function. Insertions and deletions can be substantial, such as the case of a truncation of a substantial fragment of the sequence, or in the fusion of additional sequence, either internally or at N or C terminal.

One aspect of the invention pertains to isolated nucleic acid molecules that encode modified triterpene methyltransferase polypeptides or biologically active portions thereof. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule of the present invention, e.g., a nucleic acid molecule that encodes a polypeptide set forth in SEQ ID NO:2, or having the nucleotide sequence as set forth in SEQ ID NO:1, or a portion thereof, can be isolated using standard molecular biology techniques and the sequence information provided herein.

A nucleic acid molecule of the invention can be amplified using cDNA, mRNA or alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer. In some embodiments, an isolated nucleic acid molecule of the invention comprises a nucleic acid molecule encoding a polypeptide set forth in SEQ ID NO:2 or conservative variant thereof, or is a complement of a nucleotide sequence encoding a polypeptide set forth in SEQ ID NO:2 or conservative variant thereof, or having the nucleotide sequence set forth in SEQ ID NO:1. In still another embodiment, an isolated nucleic acid molecule of the invention comprises a nucleotide sequence set forth in SEQ ID NO:1, a nucleotide sequence that is at least about 50%, 52%, 55%, 60%, 62%, 65%, 70%, 75%, 78%, 80%, 85%, 88%, 90%, 95%, 97%, 98% or more identical to SEQ ID NO:1 or a nucleotide sequence encoding a polypeptide set forth in SEQ ID NO:2, or a portion of any of these nucleotide sequences.

In addition to the nucleotide sequences encoding a polypeptide set forth in SEQ ID NO:2, or having the nucleotide sequence set forth in SEQ ID NO:1, it will be appreciated by those skilled in the art that DNA sequence polymorphisms that lead to changes in the amino acid sequences of the proteins may exist within a population. Such genetic polymorphisms may exist among individuals within a population due to natural allelic variation. Such natural allelic variations include both functional and non-functional proteins and can typically result in 1-5% variance in the nucleotide sequence of a gene. Any and all such nucleotide variations and resulting amino acid polymorphisms in genes that are the result of natural allelic variation and that do not alter the functional activity of a protein are intended to be within the scope of the invention.

Accordingly, in another embodiment, an isolated nucleic acid molecule of the invention hybridizes under stringent conditions to a nucleic acid molecule comprising the nucleotide sequence encoding a polypeptide set forth in SEQ ID NO:2, or having the nucleotide sequence set forth in SEQ ID NO:1. In other embodiments, the nucleic acid molecule is at least 30, 50, 100, 150, 200, 250, 300, 350, 400, 450, 500, 550, 600, 650, 70, 750, 800, 850, 900, 950, 1000, 1050, 1100 or 1140 nucleotides in length. Nucleic acid molecules are "hybridizable" to each other when at least one strand of one polynucleotide can anneal to another polynucleotide under defined stringency conditions. Stringency of hybridization is determined, e.g., by (a) the temperature at which hybridization and/or washing is performed, and (b) the ionic strength and polarity (e.g., formamide) of the hybridization and washing solutions, as well as other parameters. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarity between the hybridizing sequences (1×SSC is 0.15 M NaCl, 0.015 M Na citrate). Nucleic acid molecules that hybridize include those which anneal under suitable stringency conditions and which encode polypeptides or enzymes having the same function, such as the ability to catalyze the conversion of a triterpene (e.g., botryococcene) to a methylated triterpene (e.g., tetramethylated botryococcene), of the invention. Further, the term "hybridizes under stringent conditions" is intended to describe conditions for hybridization and washing under which nucleotide sequences at least 30%, 40%, 50%, or 60% homologous to each other typically remain hybridized to each other. Preferably, the conditions are such that sequences at least about 70%, more preferably at least about 80%, even more preferably at least about 85% or 90% homologous to each other typically remain hybridized to each other. In some cases, an isolated nucleic acid molecule of the invention that hybridizes under stringent conditions to a nucleic acid sequence encoding a polypeptide set forth in any of SEQ ID NO:2, or having the nucleotide sequence set forth in SEQ ID NO: 1, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). Preferably the nucleic acid molecule that hybridizes, hybridizes to at least 30%, 40%, 50%, 60%, 70%, 80%, 85% or 90% of the length of a nucleic acid molecule consisting of SEQ ID NO:1 under stringent conditions. More preferably the nucleic acid molecule that hybridizes, hybridizes to at least about 80%, even more preferably at least about 85% or 90% of the length of a nucleic acid molecule consisting of SEQ ID NO: 1. Preferably the nucleic acid molecule that hybridizes encodes a polypeptide having triterpene methyltransferase activity.

The skilled artisan will appreciate that changes can be introduced by mutation into the nucleotide sequences of any nucleic acid sequence encoding a polypeptide set forth in SEQ ID NO:2, or having the nucleotide sequence set forth in SEQ ID NO:1, thereby leading to changes in the amino acid sequence of the encoded proteins. In some cases the alteration will lead to altered function of the polypeptide. In other cases the change will not alter the functional ability of the encoded polypeptide. In general, substitutions that do not alter the function of a polypeptide include nucleotide substitutions leading to amino acid substitutions at "non-essential" amino acid residues. Generally these substitutions can be made in, for example, the sequence encoding a polypeptide set forth in SEQ ID NO:2, or having the nucleotide sequence set forth in SEQ ID NO:1, without altering the ability of the enzyme to catalyze the methylation of a terpene. A "non-essential" amino acid residue is a residue that can be altered from the parent sequence without altering the biological activity of the resulting polypeptide, e.g., catalyzing the conversion of methane to methanol.

Also contemplated are those situations where it is desirable to alter the activity of a parent polypeptide such that the polypeptide has new or increased activity on a particular substrate. It is understood that these amino acid substitutions will generally not constitute "conservative" substitutions. Instead, these substitutions constitute non-conservative substitutions introduced into a sequence in order to obtain a new or improved activity.

It is also understood that an isolated nucleic acid molecule encoding a polypeptide homologous to the polypeptide of SEQ ID NO:2 can be created by introducing one or more nucleotide substitutions, additions or deletions into the nucleotide sequence encoding the particular polypeptide, such that one or more amino acid substitutions, additions or deletions are introduced into the encoded protein. Mutations can be introduced into the nucleic acid sequence by standard techniques, such as site-directed mutagenesis and PCR-mediated mutagenesis. In contrast to those positions where it may be desirable to make a non-conservative amino acid substitutions (see above), in some positions it is preferable to make conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Mutational methods of generating diversity include, for example, site-directed mutagenesis (Ling et al. (1997) "Approaches to DNA mutagenesis: an overview" *Anal Brioche.* 254(2): 157-178; Dale et al. (1996) "Oligonucleotide-directed random mutagenesis using the phosphorothioate method" *Methods Mol. Biol.* 57:369-374; Smith (1985) "In vitro mutagenesis" *Ann. Rev. Genet.* 19:423-462; Botstein & Shortle (1985) "Strategies and applications of in vitro mutagenesis" *Science* 229:1193-1201; Carter (1986) "Site-directed mutagenesis" *Biochem. J.* 237:1-7; and Kunkel (1987) "The efficiency of oligonucleotide directed mutagenesis" in *Nucleic Acids & Molecular Biology* (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" *Proc. Natl. Acad. Sci. USA* 82:488-492; Kunkel et al. (1987) "Rapid and efficient site-specific mutagenesis without phenotypic selection" *Methods in Enzymol.* 154, 367-382; and Bass et al. (1988) "Mutant Trp repressors with new DNA-binding specificities" *Science* 242:240-245); oligonucleotide-directed mutagenesis (*Methods in Enzymol.* 100: 468-500 (1983); *Methods in Enzymol.* 154: 329-350 (1987); Zoller & Smith (1982) "Oligonucleotide-directed mutagenesis using M13-derived vectors: an efficient and general procedure for the production of point mutations in any DNA fragment" *Nucleic Acids Res.* 10:6487-6500; Zoller & Smith (1983) "Oligonucleotide-directed mutagenesis of DNA fragments cloned into M13 vectors" *Methods in Enzymol.* 100: 468-500; and Zoller & Smith (1987) "Oligonucleotide-directed mutagenesis: a simple method using two oligonucleotide primers and a single-stranded DNA template" *Methods in Enzymol.* 154:329-350); phosphorothioate-modified DNA mutagenesis (Taylor et al. (1985) "The use of phosphorothioate-modified DNA in restriction enzyme reactions to prepare nicked DNA" *Nucl. Acids Res.* 13: 8749-8764; Taylor et al. (1985) "The rapid generation of oligonucleotide-directed mutations at high frequency using phosphorothioate-modified DNA" *Nucl. Acids Res.* 13: 8765-8787; Nakamaye & Eckstein (1986) "Inhibition of restriction endonuclease Nci I cleavage by phosphorothioate groups and its application to oligonucleotide-directed mutagenesis" *Nucl. Acids Res.* 14: 9679-9698; Sayers et al. (1988) "Y-T Exonucleases in phosphorothioate-based oligonucleotide-directed mutagenesis" *Nucl. Acids Res.* 16:791-802; and Sayers et al. (1988) "Strand specific cleavage of phosphorothioate-containing DNA by reaction with restriction endonucleases in the presence of ethidium bromide" *Nucl. Acids Res.* 16: 803-814); mutagenesis using gapped duplex DNA (Kramer et al. (1984) "The gapped duplex DNA approach to oligonucleotide-directed mutation construction" *Nucl. Acids Res.* 12: 9441-9456; Kramer & Fritz (1987) *Methods in Enzymol.* "Oligonucleotide-directed construction of mutations via gapped duplex DNA" 154:350-367; Kramer et al. (1988) "Improved enzymatic in vitro reactions in the gapped duplex DNA approach to oligonucleotide-directed construction of mutations" *Nucl. Acids Res.* 16: 7207; and Fritz et al. (1988) "Oligonucleotide-directed construction of mutations: a gapped duplex DNA procedure without enzymatic reactions in vitro" *Nucl. Acids Res.* 16: 6987-6999) (each of which is incorporated in its entirety by reference).

Additional suitable methods include point mismatch repair (Kramer et al. (1984) "Point Mismatch Repair" *Cell* 38:879-887), mutagenesis using repair-deficient host strains (Carter et al. (1985) "Improved oligonucleotide site-directed mutagenesis using M13 vectors" *Nucl. Acids Res.* 13: 4431-4443; and Carter (1987) "Improved oligonucleotide-directed mutagenesis using M13 vectors" *Methods in Enzymol.* 154: 382-403), deletion mutagenesis (Eghtedarzadeh & Henikoff (1986) "Use of oligonucleotides to generate large deletions" *Nucl. Acids Res.* 14: 5115), restriction-selection and restriction-purification (Wells et al. (1986) "Importance of hydrogen-bond formation in stabilizing the transition state of subtilisin" *Phil. Trans. R. Soc. Lond. A* 317: 415-423), mutagenesis by total gene synthesis (Nambiar et al. (1984) "Total synthesis and cloning of a gene coding for the ribonuclease S protein" *Science* 223: 1299-1301; Sakamar and Khorana (1988) "Total synthesis and expression of a gene for the a-subunit of bovine rod outer segment guanine nucleotide-binding protein (transducin)" *Nucl. Acids Res.* 14: 6361-6372; Wells et al. (1985) "Cassette mutagenesis: an efficient method for generation of multiple mutations at defined sites" *Gene* 34:315-323; and Grundstrom et al. (1985) "Oligonucleotide-directed mutagenesis by microscale shotgun gene synthesis" *Nucl. Acids Res.* 13: 3305-3316); double-strand break repair (Mandecki (1986); Arnold (1993) "Protein engineering for unusual environments" Current Opinion in Biotechnology 4:450-455; and "Oligonucleotide-directed double-strand break repair in plasmids of *Escherichia coli*: a method for site-specific mutagenesis" *Proc. Natl. Acad. Sci. USA,* 83:7177-7181) (each of which is incorporated in its entirety by reference). Additional details on many of the above methods can be found in Methods in Enzymology Volume 154, which also describes useful controls for trouble-shooting problems with various mutagenesis methods.

Additional details regarding various diversity generating methods can be found in the following U.S. patents, PCT publications, and EPO publications: U.S. Pat. No. 5,605,793 to Stemmer (Feb. 25, 1997), "Methods for In vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/13487 by Stemmer et al., "Methods for Optimization of Gene Therapy by Recursive Sequence Shuffling and Selection;" WO 00/00632, "Methods for Generating Highly Diverse Libraries;" WO 00/09679, "Methods for Obtaining in vitro Recombined Polynucleotide Sequence Banks and Resulting Sequences;" WO 98/42832 by Arnold et al., "Recombination of Polynucleotide Sequences Using Random or Defined Primers;" WO 99/29902 by Arnold et al., "Method for Creating Polynucleotide and Polypeptide Sequences;" WO 98/41653 by Vind, "An in vitro Method for Construction of a DNA Library;" WO 98/41622 by Borchert et al., "Method for Constructing a Library Using DNA Shuffling;" WO 98/42727 by Pati and Zarling, "Sequence Alterations using Homologous Recombination;" WO 00/18906 by Patten et al., "Shuffling of Codon-Altered Genes;" WO 00/04190 by del Cardayre et al. "Evolution of Whole Cells and Organisms by Recursive Recombination;" WO 00/42561 by Crameri et al., "Oligonucleotide Mediated Nucleic Acid Recombination;" WO 00/42559 by Selifonov and Stemmer "Methods of Populating Data Structures for Use in Evolutionary Simulations;" WO 00/42560 by Selifonov et al., "Methods for Making Character Strings, Polynucleotides & Polypeptides Having Desired Characteristics;" WO 01/23401 by Welch et al., "Use of Codon-Varied Oligonucleotide Synthesis for Synthetic Shuffling;" and WO 01/64864 "Single-Stranded Nucleic Acid Template-Mediated Recombination and Nucleic Acid Fragment Isolation" by Affholter (each of which is incorporated in its entirety by reference). The QUICKCHANGE™ protocol marketed by Stratagene of San Diego, Calif. is one specific method known to those skilled in the art for introducing site-directed mutations. This method relies on the use of oligo or DNA primer pairs, harboring specific DNA sequence changes to be introduced, annealed to the target DNA or gene to be modified. Copies of modified DNA/gene are amplified by standard PCR methodology. Confirmation of alteration of the target DNA sequence is verifiable by automated DNA sequencing.

Also provided are recombinant constructs comprising one or more of the nucleic acid sequences as broadly described above. The constructs comprise a vector, such as, a plasmid, a cosmid, a phage, a virus, a bacterial artificial chromosome (BAC), a yeast artificial chromosome (YAC), or the like, into which a nucleic acid sequence of the invention has been inserted, in a forward or reverse orientation. In a preferred aspect of this embodiment, the construct further comprises regulatory sequences including, for example, a promoter operably linked to the sequence. Large numbers of suitable vectors and promoters are known to those of skill in the art, and are commercially available.

Accordingly, in other embodiments, vectors that comprise a nucleic acid molecule of the invention are provided. In other embodiments, host cells transfected with a nucleic acid molecule of the invention, or a vector that comprises a nucleic acid molecule of the invention, are provided. Host cells include eukaryotic cells such as yeast cells, insect cells, animal cells, or plant cells (e.g., algal cells or terrestrial plant cells). Host cells also include prokaryotic cells such as bacterial cells.

The terms "vector", "vector construct" and "expression vector" mean the vehicle by which a DNA or RNA sequence (e.g. a foreign gene) can be introduced into a host cell, so as to transform the host and promote expression (e.g. transcription and translation) of the introduced sequence. Vectors typically comprise the DNA of a transmissible agent, into which foreign DNA encoding a protein is inserted by restriction enzyme technology. A common type of vector is a "plasmid", which generally is a self-contained molecule of double-stranded DNA that can readily accept additional (foreign) DNA and which can readily introduced into a suitable host cell. A large number of vectors, including plasmid and viral vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), pMAL plasmids (New England Biolabs, Beverly, Mass.), and Ti plasmid vectors, and many appropriate host cells, using methods disclosed or cited herein or otherwise known to those skilled in the relevant art. Vectors can also be selected and designed such that the polypeptide encoded by the introduced sequence is localized in the cytoplasm or targeted to particular cellular organelle, e.g., targeted to a chloroplast in a plant cell. For example a protein may be targeted to a chloroplast by appending a chloroplast targeting sequence, e.g., ATGGCTTCCTC-TATGCTCTCCTCCGCCGCTGTGGTT ACATCCCCG-GCTCAGGCCACCATGGTCGCTCCATTCACCG GCTTGAAGTCATCCG CTGCATTCCCGGTCACCCG-CAAGACCAACAAGGACATCACTTCCATCGCAAGCA ACGGGGGAAGATCTAGCTGCATGAAG-GAGCTCGGCGCGCCT (SEQ ID NO: 44), to the 5' translation start sequence of another gene. The chloroplast targeting sequence encodes for N-terminal amino acid extension MASSMLSSAAVVTSPAQATMVAPFTGLKSSAAFP VTRKTNKDITSIASNGGRSSCMKELGAP SEQ ID NO: 45) that targets the downstream protein to the chloroplast compartment. Examples of such targeting are provided by Wu et al. (2006) *Nature Biotechnology* 24:1441-1447. Recombinant cloning vectors will often include one or more replication systems for cloning or expression, one or more markers for selection in the host, e.g., antibiotic resistance, and one or more expression cassettes.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

Polynucleotides provided herein can be incorporated into any one of a variety of expression vectors suitable for expressing a polypeptide. Suitable vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated viruses, retroviruses; Ti plasmids for the incorporation and expression of DNA in plant cells, and many others. Any vector that transduces genetic material into a cell, and, if replication is desired, which is replicable and viable in the relevant host can be used.

Vectors can be employed to transform an appropriate host to permit the host to express an inventive protein or polypeptide. Examples of appropriate expression hosts include: bacterial cells, such as *E. coli, B. subtilis, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as CHO, COS, BHK, HEK 293 br Bowes melanoma; plant cells e.g., *Nicotiana tabacum*, a dicot plant species, or corn, rice or wheat, monocot plant species; algal cells e.g., *Chlamydomonas reinhardtii*; or explants of any plant tissues, e.g., leaf, stem or root segments, etc.

In bacterial systems, a number of expression vectors may be selected depending upon the use intended for the triterpene methyltransferase polypeptide. For example, when large quantities of triterpene methyltransferase polypeptide or fragments thereof are needed for commercial production or for induction of antibodies, vectors which direct high level expression of fusion proteins that are readily purified can be desirable. Such vectors include, but are not limited to, multifunctional *E. coli* cloning and expression vectors such as BLUESCRIPT™ (Stratagene), in which the triterpene methyltransferase polypeptide coding sequence may be ligated into the vector in-frame with sequences for the amino-terminal Met and the subsequent 7 residues of beta-galactosidase so that a hybrid protein is produced; pIN vectors (Van Heeke & Schuster (1989) *J. Biol. Chem.* 264: 5503-5509 incorporated herein by reference); pET vectors (Novagen, Madison Wis.); and the like.

Similarly, in the yeast *Saccharomyces cerevisiae* a number of vectors containing constitutive or inducible promoters isolated from, e.g., an alpha factor, an alcohol dehydrogenase or a PGH gene may be used for production of the triterpene methyltransferase polypeptides of the invention. For reviews, see Ausubel (supra) and Grant et al. (1987) *Methods in Enzymology* 153:516-544 (incorporated herein by reference).

Plant and algal systems may also be used for expression of triterpene methyltransferase. Transcription of sequences encoding triterpene methyltransferase may be driven by viral promoters, e.g., the 35S and 19S promoters of CaMV used alone or in combination with the omega leader sequence from TMV (Takamatsu, N. (1987) *EMBO J.* 6:307-311 incorporated herein by reference). Alternatively, plant promoters such as, e.g., the small subunit of RUBISCO or heat shock promoters may be used. (See, e.g., Coruzzi, G. et al. (1984) *EMBO J.* 3:1671-1680; Broglie, R. et al. (1984) *Science* 224:838-843; and Winter, J. et al. (1991) *Results Probl. Cell Differ.* 17:85-105, each incorporated herein by reference) For algal expression work, a strong constitutive promoter includes, e.g., a β-tubulin gene promoter (see Brunke, K J et al. (1984) *Molec. Cell. Biol.* 4: 1115-1124 incorporated herein by reference). These constructs can be introduced into plant cells, for example, by direct DNA transformation or pathogen-mediated transfection. (See, e.g., The McGraw Bill Yearbook of Science and Technology (1992) McGraw Hill, New York N.Y., pp. 191-196 incorporated herein by reference.)

Also provided are engineered host cells that are transduced (transformed or transfected) with a vector provided herein (e.g., a cloning vector or an expression vector), as well as the production of polypeptides of the invention by recombinant techniques. The vector may be, for example, a plasmid, a viral particle, a phage, etc. The engineered host cells can be cultured in conventional nutrient media modified as appropriate for activating promoters, selecting transformants, or amplifying the triterpene methyltransferase gene. Culture conditions, such as temperature, pH and the like, are those previously used with the host cell selected for expression, and will be apparent to those skilled in the art and in the references cited herein, including, e.g., Sambrook, Ausubel and Berger, as well as e.g., Freshney (1994) Culture of Animal Cells: A Manual of Basic Technique, 3rd ed. (Wiley-Liss, New York), and the references cited therein, incorporated herein by reference.

In other embodiments, methods for producing a cell that converts a triterpene to a methylated triterpene are provided. Such methods generally include: (a) transforming a cell with an isolated nucleic acid molecule encoding a triterpene methyltransferase polypeptide, e.g., a nucleic acid molecule of this invention encoding e.g., a polypeptide comprising SEQ ID NO: 2, a variant, preferably a conservative variant, of SEQ ID NO: 2, a polypeptide that is at least 37% identical to SEQ ID NO: 2 or a fragment of SEQ ID NO: 2.

In other embodiments, methods for selecting a cell that converts a triterpene to a methylated triterpene are provided. The methods generally include: (a) providing a cell containing a nucleic acid construct that includes a nucleotide sequence that encodes a triterpene methyltransferase polypeptide. The methods further include (b) culturing the cell in the presence of a suitable triterpene and under conditions where the triterpene methyltransferase is expressed at an effective level; and (c) detecting the production of a methylated triterpene.

In other embodiments, methods for producing a methylated triterpene are provided. In general, a methylated triterpene produced by a method of the invention can include, for example, monomethyl-botryococcene, dimethyl-botryococcene, trimethyl-botryococcene, tetramethyl-botryococcene, monomethyl-squalene, dimethyl-squalene, trimethyl-squalene, and tetramethyl-squalene.

In one aspect, the methods for producing a methylated triterpene comprise providing a metabolizable carbon source to a host cell transfected with a nucleic acid molecule of this invention that encodes a triterpene methyltransferase under conditions sufficient for production of a methylated triterpene. Preferably the triterpene methyltransferase comprises the amino acid sequence set forth in SEQ ID NO: 2, a conservative variant thereof, e.g., a polypeptide that is at least 37% identical to the full-length of SEQ ID NO: 2, or fragments thereof having triterpene methyltransferase activity, e.g., a fragment thereof comprising SMT-II, SEQ ID NO: 17. Optionally, the methylated triterpenes produced by the host cells are isolated. The host cell may be, for example, a cell in culture or it may be a cell which is part of an organism such as a transfected cell in a terrestrial plant. The metabolizable carbon source may be, for example, carbon dioxide, so that in a transfected plant host cell expressing an effect level of triterpene methyltransferase and having other appropriate intracellular enzymes, the carbon dioxide fixed in the process of photosynthesis can be diverted to triterpene synthesis and, ultimately, leads to accumulation of methylated triterpenes. In addition to transfection with triterpene methyltransferase-encoding nucleic acid molecule, such plant cells may also be cotransfected with nucleic acid molecules encoding for one or more other enzymes in the triterpene synthesis pathway, such as the genes for farnesyl diphosphate synthase or a triterpene synthase such as squalene synthase or botryococcene synthase available in the art (see e.g., Anderson et al. *J. Biol. Chem.* (1989) November 15; 264(32):19176-84); Okada et al. *Arch Biochem Biophys*. (2000 January) 15; 373 (2):307-17 each incorporated herein in its entirety by reference). Plant cells for transfection include, for example algal cells such as *Botryococcus* spp. cells (e.g., *Botryococcus braunii*), *Chlamydomonas* spp. cells or terrestrial plant cells, such as a tobacco plant cell. Transfection of plant cells with exogenous genes may be directed to the cytosolic compartment, the chloroplast or both. In other embodiments, cells other than plant cells may be transformed with triterpene methyltransferase-encoding nucleic acid molecule of this invention, and optionally with nucleic acid molecules encoding one or more other enzymes involved in triterpene synthesis. These cells include, for example, prokaryotic cells such as bacteria and eukaryotic cells such as fungi or animal cells. In any of the aforementioned embodiments, the cells may also be genetically altered to enhance the production of farnesyl diphosphate and thereby provide a larger precursor pool for triterpene synthesis, such as through gene knockout, so as to eliminate or reduce diversion of farnesyl diphosphate for use in synthesis of metabolites other than triterpenes, such as sesquiterpenes, sterols, or polyprenols, or to eliminate or reduce the action of phosphatase(s) on farnesyl diphosphate. The production of triterpenes may also be enhanced by diverting other metabolic intermediates such as, e.g., isopentenyl diphosphate or dimethylallyl diphosphate (DMAPP) to the production of FPP, therein providing enhanced carbon flux to a key intermediate for the biosynthesis of triterpenes.

As discussed above, in methods for producing methylated triterpenes, transfected plant cells may be in culture or may be, for example, transfected cells in a terrestrial plant, and the metabolizable carbon source may be carbon dioxide. Alternative metabolizable carbon sources are also contemplated. For example, with plant cells or other types of cells in culture, a triterpene may be added to the culture medium so as to be acted on by the transfected cells in which an effective level of triterpene methyltransferase has been expressed. Additional metabolizable carbon sources include sugars, amino acids, fatty acids, or any other carbon substrate that the particular transfected cell can metabolize so as to provide carbon substrate for triterpene synthesis.

In another aspect, cells transfected with a nucleic acid molecule encoding a triterpene methyltransferase are cultured under conditions suitable for the expression of the triterpene methyltransferase polypeptide and an extract rich in triterpene methyltransferase is then prepared. This extract may be, for example, a cell paste or tissue homogenate, or it may be, for example, a purified or partially purified preparation of triterpene methyltransferase. A triterpene substrate is then exposed to the extract rich in triterpene methyltransferase under conditions which allow for production of methylated triterpenes. The methylation may be via a batch process or a continuous process. Optionally the methylated triterpenes may then be isolated.

As previously discussed, general texts which describe molecular biological techniques useful herein, including transformation techniques, the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel") (each of which is incorporated in its entirety by reference). Examples of protocols sufficient to direct persons of skill through in vitro amplification methods, including the polymerase chain reaction (PCR), the ligase chain reaction (LCR), Qβ-replicase amplification and other RNA polymerase mediated techniques (e.g., NASBA), e.g., for the production of the homologous nucleic acids of the invention are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; *The Journal Of NIH Research* (1991) 3: 81-94; Kwoh et al. (1989) *Proc. Natl. Acad. Sci. USA* 86: 1173; Guatelli et al. (1990) *Proc. Nat'l. Acad. Sci. USA* 87: 1874; Lomell et al. (1989) *J. Clin. Chem.* 35: 1826; Landegren et al. (1988) *Science* 241: 1077-1080; Van Brunt (1990) *Biotechnology* 8: 291-294; Wu and Wallace (1989) Gene 4:560; Barringer et al. (1990) *Gene* 89:117; and Sooknanan and Malek (1995) *Biotechnology* 13: 563-564 (each of which is incorporated by reference). Improved methods for cloning in vitro amplified nucleic acids are described in Wallace et al., U.S. Pat. No. 5,426,039 incorporated herein by reference. Improved methods for amplifying large nucleic acids by PCR are summarized in Cheng et al. (1994) *Nature* 369: 684-685, and the references cited therein, (incorporated in its entirety by reference herein), in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

These and other embodiments of the present invention will readily occur to those of ordinary skill in the art in view of the disclosure herein, and are specifically contemplated.

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications fall within the scope of the appended claims.

EXAMPLES

Example 1

Isolation of the *Botryococcus braunii* Triterpene Methyltransferase Gene

In brief, total RNA was isolated from *Botryococcus braunii* cell cultures at several stages of a growth cycle, and the polyA$^+$ mRNA subfraction subsequently isolated by oligo (dT) cellulose chromatography. The isolated mRNA was then converted to double stranded cDNA using an oligo(dT) primer and inserted into a lambda cloning vector using the ZAP™-cDNA synthesis kit of Strategene (La Jolla, Calif.). The cDNA library was amplified once in *E. coli* strain XL-1-Blue MRF' and aliquots of the primary library converted to plasmid DNA by in vivo plasmid excision with the ExAssist helper phage and *E. coli* strain SOLR according to the manufacturer's suggestions (Strategene). Plasmid DNA was subsequently isolated from randomly selected bacterial colonies using a WIZARD™ Plasmid Isolation Kit (Promega Inc., Madison, Wis.) and sequenced by cycle sequencing using an ABI PRISM™ 310 Genetic Analyzer according to the manufacturer's recommendations as previously described (Okada et al., *Arch. Biochem. Biophys.*, 373: 307-317, 2000). The DNA sequences obtained were manually screened against the Genbank database (NCBI website: www.ncbi.nlm.nih.gov) using the blastx search function (www.ncbi.nlm.nih.gov/BLAST). The triterpene methyltransferase gene was noted because of its sequence similarity to plant sterol methyltransferase genes. For instance, the *B. braunii* TMT cDNA exhibits about 41% sequence identity to a rice (*Oryza sativa*) 24-methylene lophenol C24(1)methyltransferase (GenBank accession AAC34989), about 40% identity to an *Arabidopsis thaliana* 24-sterol C-methyltransferase (GenBank accession AAM91592), and contains consensus sequences for S-adenosyl methionine (SAM) binding domains (Martin et al., *Current Opinion in Structural Biology*, 13: 140-140, 2003). The DNA sequence of the entire triterpene methyltransferase (TMT) cDNA clone (FIG. 1) yielded a putative full-length cDNA clone coding for a 379 amino acid protein having a predicted molecular size of 41,780 daltons, as shown in FIG. 2. The putative triterpene methyltransferase (TMT) gene has sequence similarity to other known sterol methyltransferases (SMT). Shown in FIG. 3 is a comparison of putative SAM (S-adenosyl methionine) and SMT (sterol methyltransferase specific) binding motifs in terpene methyltransferase genes from a variety of plants and *Botryococcus braunii* triterpene methyltranferase.

Example 2

Functional Characterization of the *B. braunii* Triterpene Methyltransferase

The entire open reading frame, ORF, region of the TMT cDNA was amplified using standard PCR conditions with a forward primer (5'CGGAATTCATGGCCCTGGATCTTC TTTCATCC 3' (SEQ ID NO:3), containing an EcoR1 restriction site noted in bold), a reverse primer (5' GGG-GAAGCTTTTACTCTGGCTTTTGGAAGATCAG 3' (SEQ ID NO:4), containing an HindIII restriction site in bold) and the corresponding pBS plasmid vector harboring the original TMT cDNA clone. The amplified cDNA fragment was digested with the restriction enzymes EcoRI and HindIII, and the digested DNA fragment isolated by agarose gel electrophoresis. The isolated fragment was subsequently cloned into the corresponding restriction sites of the pET43 expression vector (Novagen, Madison Wis.). The pET43 expression vector includes a NUS protein fused in-frame with the amino terminus of the TMT cDNA, creating a fusion protein that was found important for obtaining expression of soluble, hybrid protein in bacteria. The recombinant pET43 vector was transformed into *E. coli* strain BL21(DE3) according to the manufacturer's recommendations (Novagen) and the engineered bacteria selected for growth in the presence of a suitable antibiotic selection marker.

*E. coli* harboring the recombinant plasmid were grown in liquid LB broth at 37° C. with vigorous shaking until the cultures reached an optical density of ~0.5 (OD600 nm), then expression of the TMT cDNA was induced by addition of 1 mM isopropylthio-B-D-galactoside (IPTG) and the cultures allowed to incubate for an addition 6 to 20 hours with shaking at room temperature. One hundred ml of the culture were subsequently collected by centrifugation at 4,000 g for 10 min, resuspended in 10 ml of lysis buffer (50 mM Tris-HCl, 2 mM MgCl$_2$, 2 mM β-mercaptoethanol, 1 mM EDTA, 5% (v/v) glycerol, pH 7.5) by vortexing, then sonicated 5 times for 20 seconds with a microprobe sonicator at 60% maximum power. The samples were cooled on ice for 2 min between sonication treatments. The sonicate was centrifuged at 16,000 g for 15 min at 4° C. and 10-50 µl of the supernatant (corresponding to 30-100 µg of total soluble protein) used for the methyltransferase assays.

Figure 4:
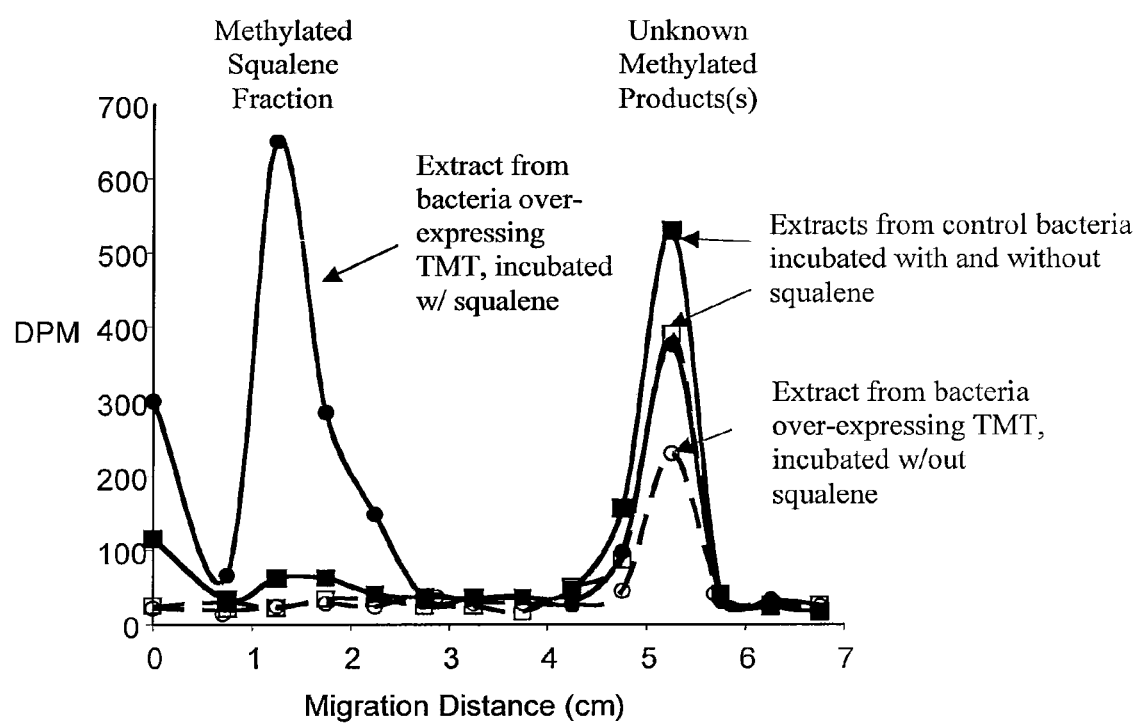
FIG. 4 shows TLC separation of reaction products generated upon incubation of extracts from bacteria over-expressing the TMT gene with (filled circle symbols) and without squalene (open circle symbols). Extracts of bacteria transformed with empty vector (no TMT gene) were also incubated under identical conditions with (filled square symbols) and without (open square symbols) squalene addition. Reactions products extracted from the respective reactions were separated by reverse phase TLC and the radioactivity associated with the indicated zones determined by scintillation counting.

Typical TMT enzyme assays consisted of preparing the squalene substrate mixture by adding 1 µl of commercially available squalene (Sigma Chemical Company) with 49 µl of a 10 mM Hepes buffer, pH 7.5, 0.02% Tween-80 solution, and incubating the mixture in a sonicating water bath for 10 min. The mixture was cooled to room temperature before adding 0.5 µl of S-adenosyl-L-[methyl-3H]methionine (84 Ci/mmol) (GE Healthcare) and up to 50 µl of the *E. coli* supernatant prepared as above. Final reaction volumes were adjusted to 100 µl with 10 mM Hepes pH 7.5 buffer. Control reactions consisted of reaction buffer only (no squalene added). The reactions were incubated for 30 min at room temperature, then stopped by the addition of 100 µl of 10% KOH in methanol, followed by extraction with 400 µl of hexane. Aliquots of the hexane extract were subsequently spotted onto C18 reverse phase TLC plates and the plates developed in acetonitrile. Half centimeter zones of the plates were then scraped and the radioactivity associated with each zone determined by scintillation counting (FIG. 4).

Figure 5:
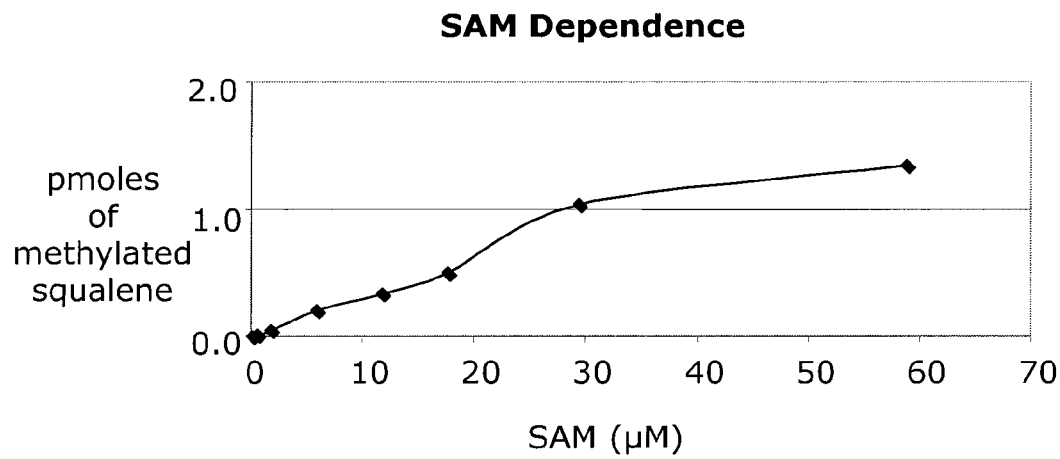
FIG. 5 illustrates that methylated squalene formation is S-adenosylmethionine (SAM) dependent. An extract from bacteria over-expressing the TMT cDNA was incubated with 20 mM squalene and the indicated concentrations of (3H-methyl)-SAM for 30 min before separation of the methylated squalene products by reverse phase TLC. Zones of the TLC plate corresponding to where the methylated squalene migrated were scraped into scintillation vials, the radioactivity associated with these zone determined by scintillation counting and the amount of methylated squalene formed calculated on the basis of the radioactivity incorporated.
Figure 6:
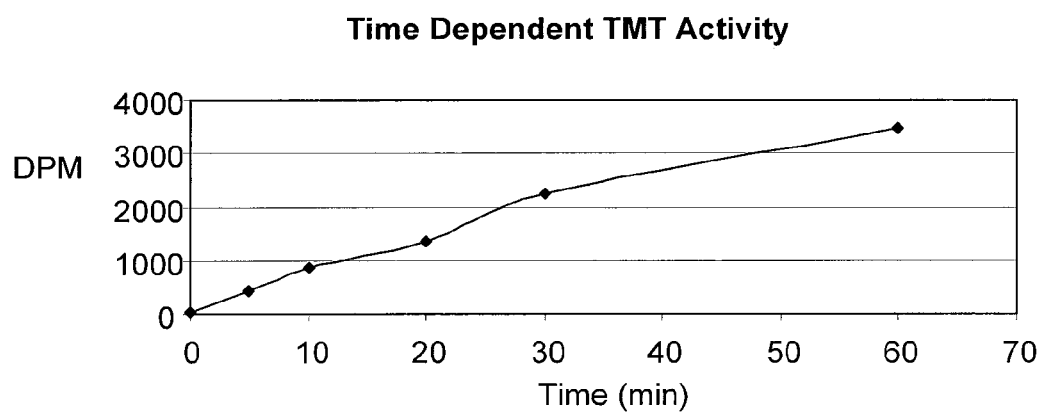
FIG. 6 shows the time dependency of TMT activity.
Figure 7:
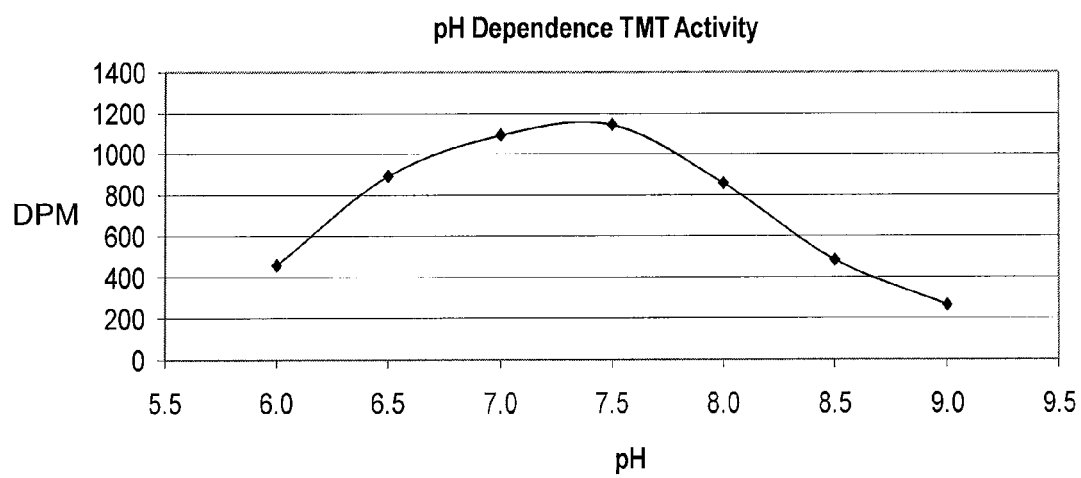
FIG. 7 illustrates the pH dependency of TMT activity.
Figure 8:
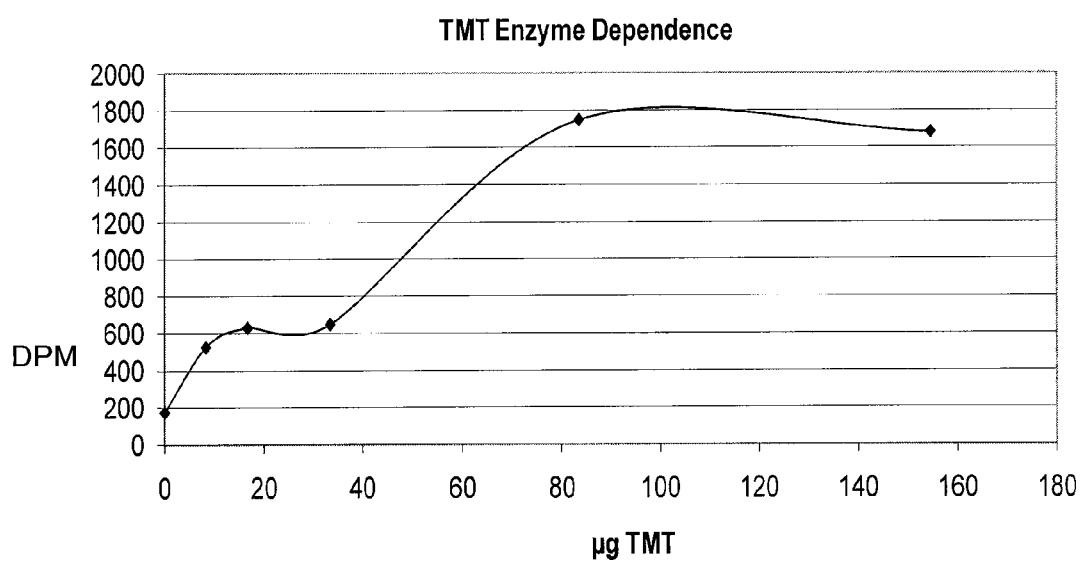
FIG. 8 shows that TMT activity is extract amount dependent.
Figure 9:
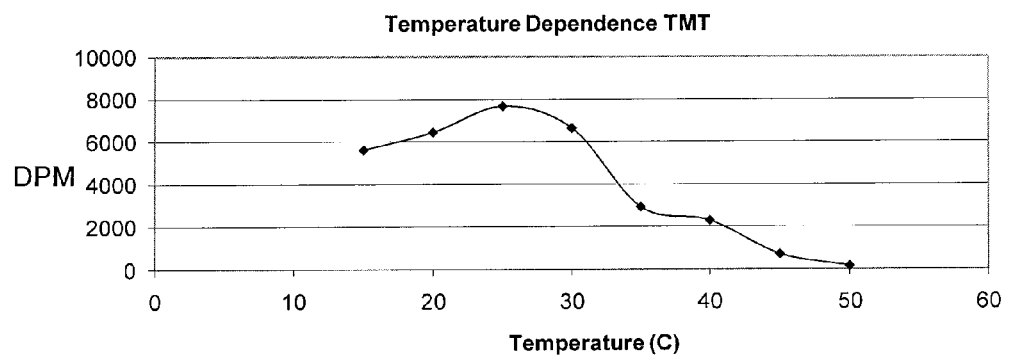
FIG. 9 shows the temperature dependency of TMT activity.

Control experiments included bacteria transformed with the pET43 vector without the TMT cDNA (empty vector controls) and incubations of bacterial extracts with and without squalene. As shown in FIG. 4, all the assay incubations, including those extracts from bacteria expressing the TMT gene, generated a radiolabeled product that migrated with an Rf>0.7. This reaction product(s) was formed regardless of squalene and expression of the TMT gene. Only the experimental sample consisting of the extract from bacteria induced to express the TMT gene was able to generate a unique reaction product from squalene, a reaction product that migrated with an Rf approximately equal to 0.15, consistent with that for tetramethylated squalenes as reported by Achitouv et al. (*Phytochemistry*, 65: 3159-3165, 2004). Formation of the methylated squalene product was not only dependent upon the addition of squalene to the reaction, but S-adenosylmethionine, the methyl donor substrate, as well (FIG. 5). Additional characterization of the TMT enzyme activity demonstrated that formation of the methylated squalene was time and extract amount dependent (FIGS. 6 and 7, respectively), and optimal at pH 7.5 and 25° C. (FIGS. 8 and 9 respectively).

Figure 10:
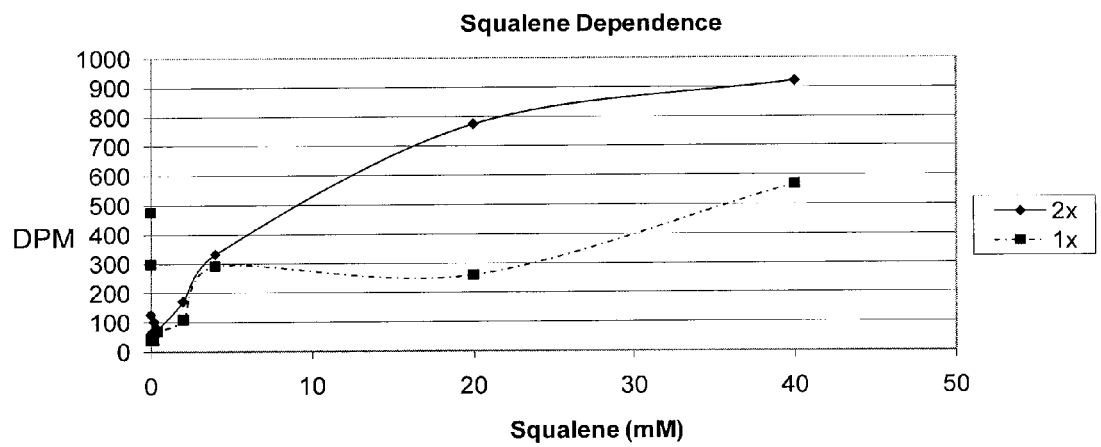
FIG. 10 illustrates the squalene substrate dependency of TMT activity.
Figure 11:
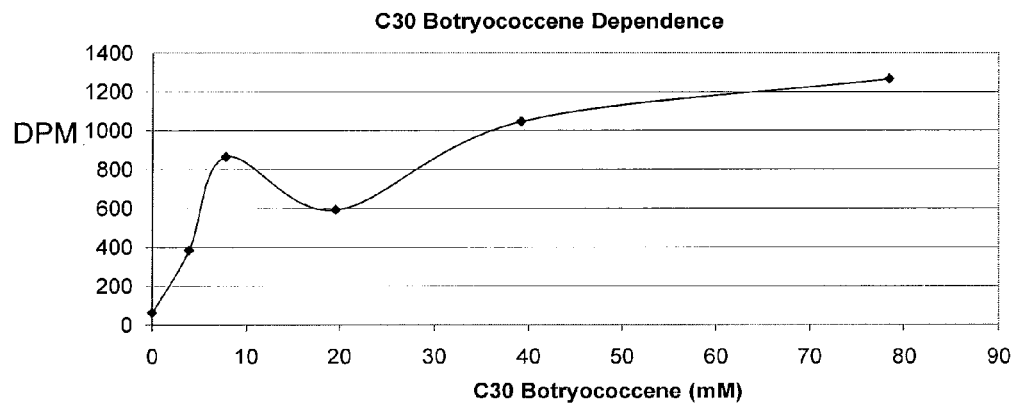
FIG. 11 shows the C30 botryococcene dependency of TMT activity.
Figure 12:
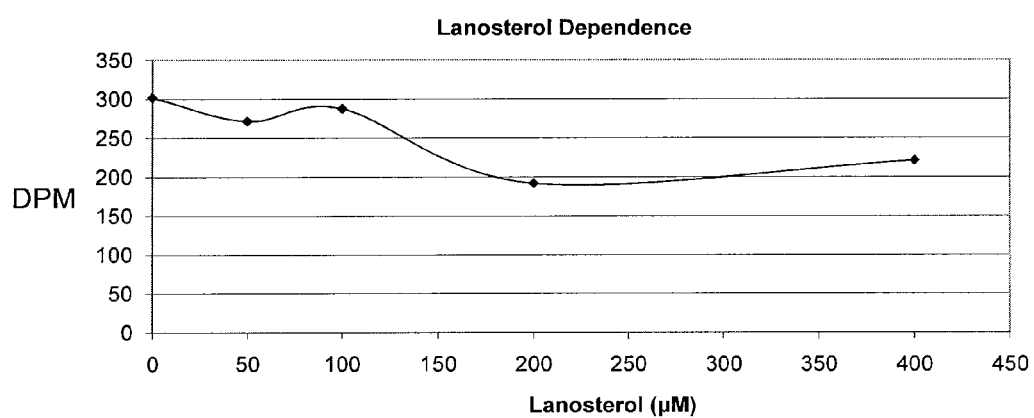
FIG. 12 illustrates the lack of lanosterol substrate dependency of TMT activity.

In addition, TMT activity is dependent on the concentration of methylated substrate, as shown in FIG. 10 for squalene and FIG. 11 for $C_{30}$ botryococcene. However, TMT does not use lanosterol as a substrate for methylation (FIG. 12). Lanosterol is a sterol typically used for sterol methyltransferase assays. Hence, TMT is not a sterol methyltransferase or a sterol methyltransferase with a broad substrate specificity, but exhibits specificity for linear triterpenes.

Example 3

Figure 13:
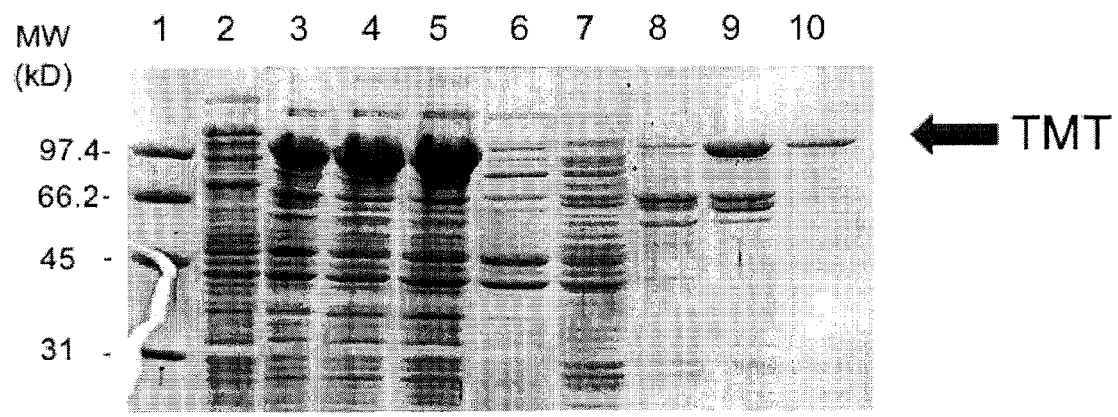
FIG. 13 demonstrates by SDS-PAGE the IPTG inducible expression of TMT in *E. coli* by the accumulation of an appropriate sized protein (approximately 120 kD) and the partial purification of the TMT protein based on a hexa-histidine tag appended to the amino terminus of the NUS-TMT construct.

Purification of the *B. braunii* Triterpene Methyltransferase Protein Over-Produced in *E. coli* Expressing the *B. braunii* Triterpene Methyltransferase Gene FIG. 13 shows the IPTG inducible expression of the TMT gene in *E. coli* by the accumulation of an appropriate sized protein (approximately 120 kD) and the partial purification of the TMT protein based on a hexa-histidine tag appended to the amino terminus of the NUS-TMT construct.

*E. coli* cultures harboring the pET-43-TMT construct were grown to an OD600 nm of 0.5 before addition of 1.0 mM IPTG to ½ of the cultures, then returned to shaking at room temperature for 12 hours. Total protein extracts were prepared from IPTG induced and non-induced *E. coli* cells as described above, and the extract from the IPTG induced cells used for partial purification of the NUS-TMT protein. Aliquots of the cell extracts and fractions during the purification protocol were analyzed by SDS-PAGE/Coomassie Blue staining (FIG. 13). The arrow indicates the size predicted for the NUS-TMT fusion protein. Lane 1: molecular weight standards; lane 2: initial extract (soluble protein, 10,000×g supernatant) from non-induced (IPTG) cells; lane 3: extract from IPTG induced cells; lane 4: fractions from nickel affinity column chromatography: flow-through fraction; lane 5: proteins eluted with 5 mM imidazole; lane 6: proteins eluted with 25 mM imidazole; lane 7: proteins eluted with 50 mM imidazole; lane 8: proteins eluted with 100 mM imidazole; lane 9: proteins eluted with 200 mM imidazole; lane 10: proteins eluted with 500 mM imidazole.

Example 4

Figure 14:
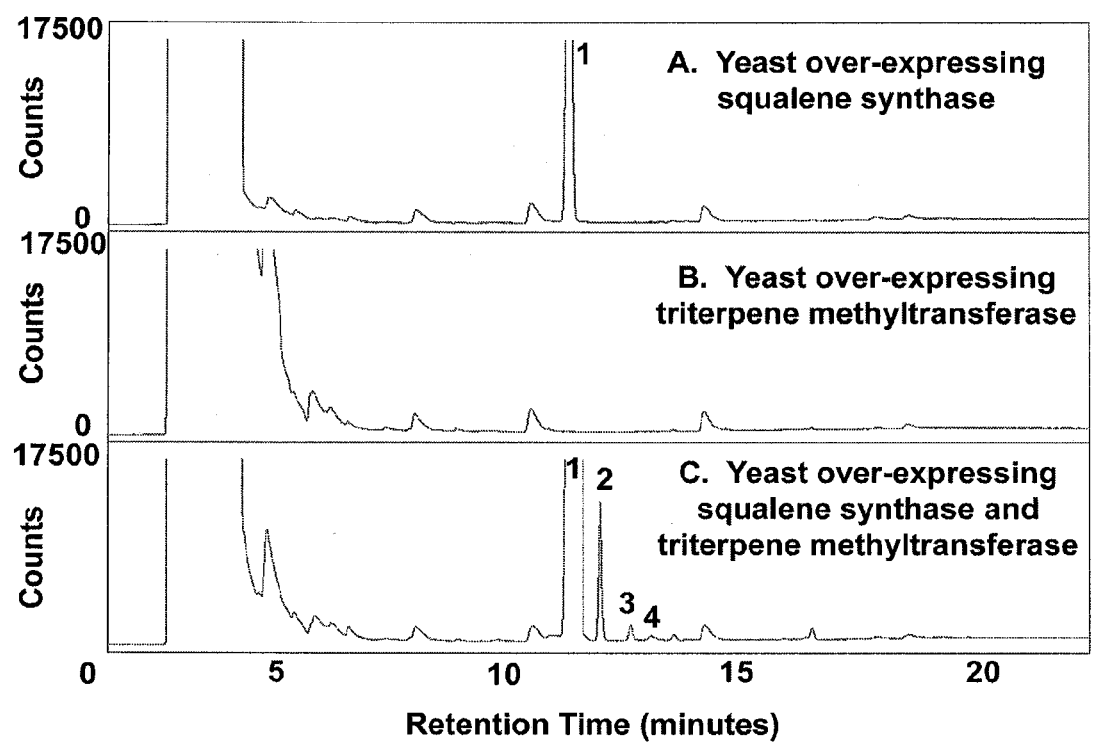
FIG. 14 shows the GC-FID detection of squalene and methylated squalenes in yeast over-expressing cDNAs for *B. braunii* squalene synthase only (A), *B. braunii* triterpene methyltransferase only (B), or both squalene synthase and triterpene methyltransferase (C). Hexane extracts of the yeast cultures were prepared, concentrated, and analyzed by GC-FID. Compound identification was based on GC retention times reported by Achitouv et al. (2004) *Phytochemistry*, 65: 3159-3165 (incorporated herein by reference).

Functional Characterization of the *B. braunii* Triterpene Methyltransferase Expressed in Yeast FIG. 14 shows the GC-FID detection of squalene and methylated squalenes in yeast over-expressing cDNAs for *B. braunii* squalene synthase only (A), *B. braunii* triterpene methyltransferase only (B), or both squalene synthase and triterpene methyltransferase (C). Hexane extracts of the yeast cultures were prepared, concentrated, and analyzed by GC-FID. Compound identification was based on GC retention times reported by Achitouv et al. (2004).

The entire open reading frame, ORF, region of the TMT cDNA was amplified using standard PCR conditions with a forward primer (5' TTGGCGCGCCAGCCCTGGATCTTC TTTCATCCTACGCTCCTGGCT (SEQ ID NO: 6), containing an AscI restriction site noted in bold), a reverse primer (5' GGGGCGGCCGCTTACTCTGGCTTTTG-GAAGATCAGCA AGTGCATGG (SEQ ID NO: 7), containing a NotI restriction site in bold) and using the pBS plasmid vector harboring the original TMT cDNA clone as template. The amplified PCR product was digested with AscI and NotI, and inserted into the corresponding sites of the yeast expression plasmid pESC-LEU behind a modified ADH1 promoter (Takahashi et al. 2007 *Biotechnology and Bioengineering* 97: 170-181 and Takahashi et al. 2007 *Journal of Biological Chemistry* 282: 31744-31754) to create the pESC-LEU-TMT construct.

A yeast expression vector harboring the *B. braunii* squalene synthase (BSS) cDNA (Okada et al., 2000) was obtained by inserting a full length BSS cDNA into the YEP352-URA vector via recombination cloning (Hartley et al., 2000 *Genome Research* 10: 1788-1795). The ORF region of the BSS cDNA was PCR amplified from a pGEM vector harboring the full-length BSS cDNA (Okada et al., 2000 *Archives of Biochemistry and Biophysics* 373: 307-317) using a reverse primer harboring an attb2 recombination site (BSS-att2-5' GGGGACCACTTTGTACAA-GAAAGCTGGGTTTAGGCGCTGAGTGAGT-GTGGGTCT AGG (SEQ ID NO: 8), att2 site in bold) and forward primer containing an attb1 recombination site (BSS-att1-5' GGGGACAAGTTTGTACAAAAAAGCAG-GCTAAAA GAATGGGGATGCTTCGCTGGGGAG, (SEQ ID NO: 9)-att1 site in bold). The PCR amplicon was purified then inserted into a YEP352-URA vector containing an attR1-[CmR-ccdB]-attR2 recombination cloning site neighboring the ADH1 promoter using the recombination cloning BP and LR reactions as recommended by the manufacturer (Gateway cloning by Invitrogen, San Diego, Calif.), creating the YEP-352-URA-BSS construct.

Constructs were then transformed into a modified yeast line (TN7) that over-accumulates squalene. TN7 was derived from CALI7-1 (Takahashi et al. 2007 *Biotechnology and Bioengineering* 97: 170-181 and Takahashi et al. 2007 *Journal of Biological Chemistry* 282: 31744-31754) by site-directed insertional mutagenesis of a TRP selection marker gene into the squalene epoxidase (ERG1) locus according to the method of X (Wang et al., 2004 *Methods* 33: 199-205; Brachmann et al., 1998 *Yeast* 14: 115-132). In brief, the ERG1 gene was amplified from yeast genomic DNA using standard PCR reaction conditions with a forward primer (5'ATGTCTGCTGTTAACGTTGCACC) (SEQ ID NO:10) and a reverse primer (5'TTAACCAATCAACTCACCAAAC) (SEQ ID NO:11), and the amplicon purified and T/A cloned into the pGEM T-easy vector according the manufacturer's directions (Promega, Madison, Wis.). The pGEM-ERG1 plasmid was subsequently digested with EcoRV to remove an internal sequence of the ERG1 gene of approximately 520 bp, and the linearized plasmid isolated by gel electrophoresis. A complete TRP1 gene (including its promoter) was also PCR amplified from the pESC-TRP plasmid using the forward primer 5' ACCTCTGACACATGCAGCTC (SEQ ID NO:12) and the reverse primer 5' GCGGTATTTTCTCCTTACGC (SEQ ID NO: 13) with PFU Taq polymerase, and the blunt-end amplicon isolated by gel purification. The isolated TRP1 blunt-end gene was then ligated into the EcoRV digested pGEM-ERG1 plasmid and recombinants verified by colony PCR using the original ERG1 and TRP1 primers noted above. The chimeric ERG1/TRP1 fragment was then amplified from one of the recombinant plasmids using the original ERG1 forward and reverse primers (see above), and the PCR amplification product purified. The linear ERG1/TRP1 PCR fragment was isolated, then transformed into CALI7-1 yeast cells using the DMSO method of Wang et al. (2004 *Methods* 33: 199-205) and transformants selected for growth on defined media (Park's media) lacking tryptophan. Insertional mutations into the genomic ERG1 gene of the transformants were verified by colony PCR screens using the original ERG1 reverse primer and the TRP1 reverse primer defined above. As expected for the insertion of the TRP1 gene into the genomic ERG1 locus, an amplification product of approximate 1,200 bp was observed, yielding a yeast line that over-accumulates squalene and designated as TN7.

Constructs YEP-URA-BSS and pESC-LEU-TMT were introduced into yeast line TN7 independently and in combination by the method of Wang et al. (2004 *Methods* 33: 199-205) and transformants selected by growth in defined media (Park's media) lacking tryptophan, leucine and/or uracil. Transformants harboring the appropriate constructs were confirmed by colony PCR methodology (www.pcrstation.com/colony-pcr), then grown in 10 to 1,000 ml of appropriate selection media for various lengths of time.

Aliquots of yeast cultures grown for 7 to 12 days were examined for their production of squalene and methylated squalenes by GC analysis (FIG. 14). Aliquots of yeast culture were mixed with an equal volume of acetone, mixed vigorously for 1 min, then allowed to stand for 5 min. The lysed cell cultures were then extracted with an equal volume of hexane, the organic layer removed, concentrated to dryness under a nitrogen stream, resuspended in a small volume of hexane, and 1-2 µl injected into a HP5890 GC equipped with a flame ionization detector, and a Restec Rtx-5 capillary column (30 m×0.25 mm). Samples were injected at 220° C. with an initial oven temperature of 200° C. for the first min, followed by a 20° C./min ramp to 280° C., then 3° C./m to 320° C., held at that temperature for a further 5 min. The FID was set to 320° C.

Example 5

Chemical Identification of Methylated Squalene Produced by Yeast Cultures Over-Expressing the *B. braunii* Triterpene Methyltransferase Gene Yeast line TN7 transformed with YEP352-URA-BSS plus pESC-LEU-TMT (a), or only with YEP352-URA-BSS (b) (as describe above) were grown for 9 days in appropriate selection media prior to hexane extraction. Aliquots of cell cultures were mixed with equal volumes of acetone, mixed vigorously, then extracted with an equal volume of hexane. The hexane extract was partially purified by silica gel chromatography with the hexane flow-through and hexane washes collected and concentrated prior to GC-MS analysis. Aliquots of the resuspended hexane extracts were examined on a Thermo-Finnigan GC/MS (DSQ) system equipped with a Restec Rtx-5 capillary column (30 m×0.25 mm). Samples were injected in the splitless mode at 220° C. with an initial oven temperature of 200° C. for 1 min followed by an 4° C./min gradient to 280° C., a 20° C./min gradient to 320° C., and a hold at 320° C. for 5 min. Mass spectra were recorded at 70 eV, scanning from 35 to 300 atomic mass units and compared with authentic standard (squalene) and literature references (Achitouv et al., 2004, *Phytochemistry* 65: 3159-3165 incorporated herein by reference). Mass spectra of peaks 1 and 2 were identified as squalene and methylsqualene, respectively.

Figure 15:
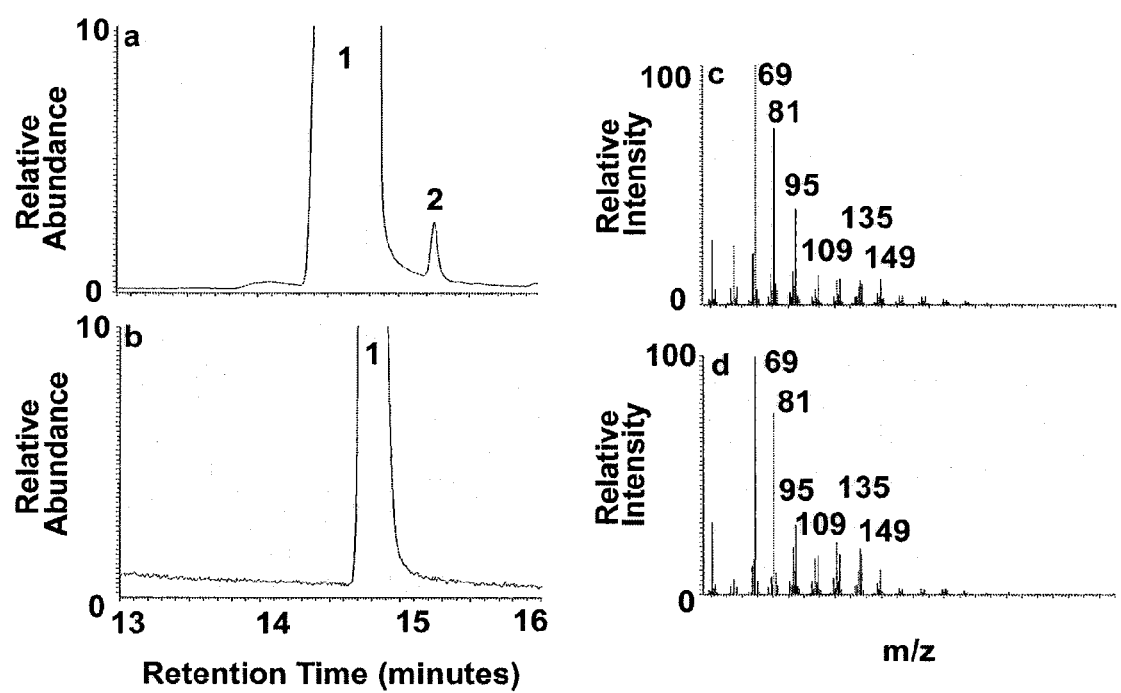
FIG. 15 shows the GC-MS detection of squalene and methylated squalene in yeast cultures over-expressing squalene synthase only (b) or squalene synthase plus triterpene methyltransferase (a).

FIG. 15 shows the GC-MS detection of squalene and methylated squalene in yeast cultures over-expressing squalene synthase only (b) or squalene synthase plus triterpene methyltransferase (a).

Example 6

Figure 16:
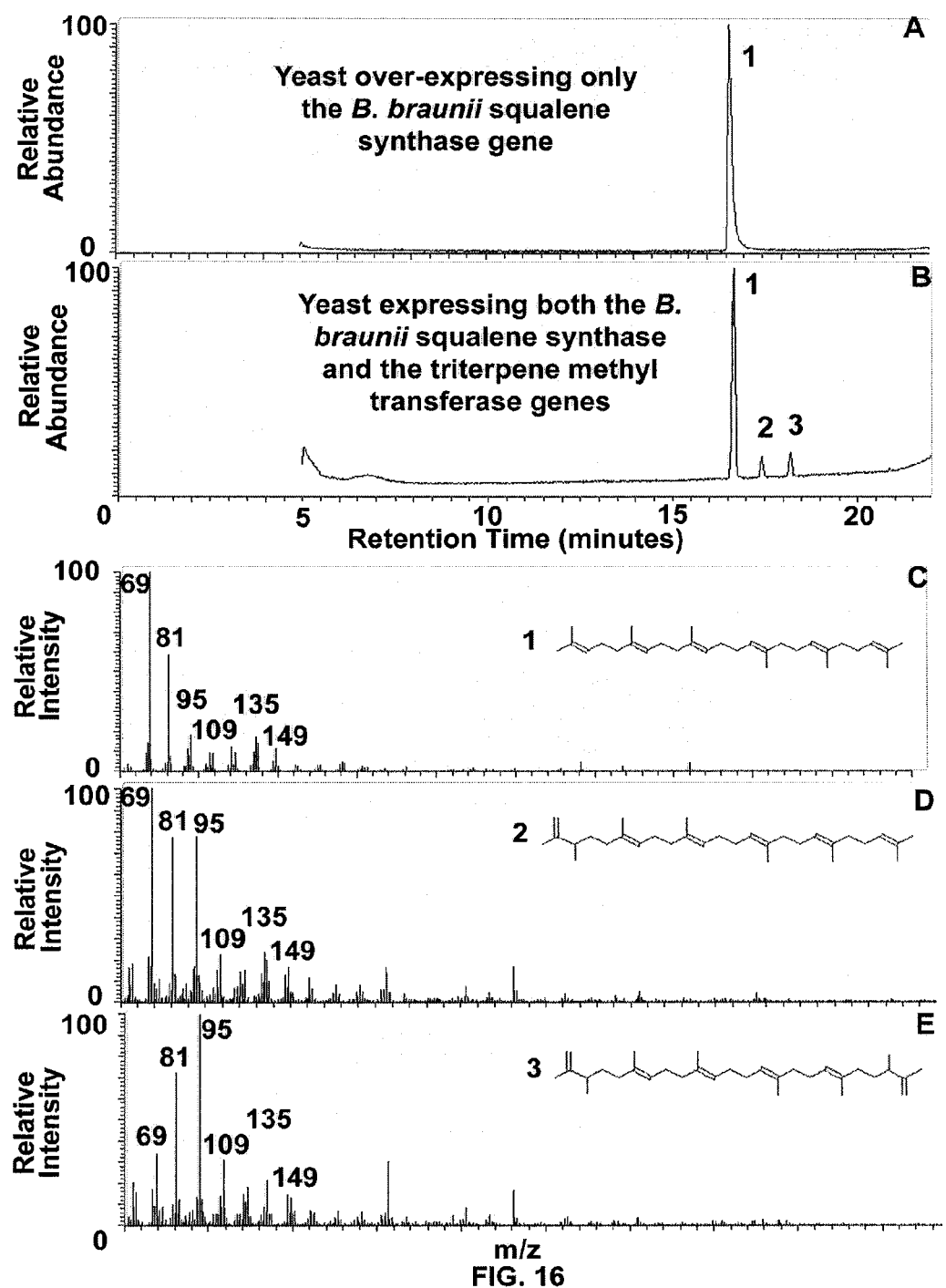
FIG. 16 depicts the lack of accumulation of methylated squalene derivatives in yeast cells over-expressing only the *B. braunii* squalene synthase (FIG. 16, panel A) or as compared to yeast cells expressing both the *B. braunii* squalene synthase and triterpene methyltransferase genes (FIG. 16, panel B).

Yeast cells over-expressing only the *B. braunii* squalene synthase (FIG. 16, panel A) or both the *B. braunii* squalene synthase and triterpene methyltransferase genes (FIG. 16, panel B) were grown for 60 days, then extract as described for Examples 4 and 5 and FIG. 14, and the accumulated compounds compared by GC-MS (panels A and B). The MS patterns for peaks 1, 2 and 3 are shown in panels C, D and E, respectively, and a chemical rendering of squalene, mono-methylated, and di-methylated squalene inserted into each of the respective panels. Only yeast over-expressing both the squalene synthase and triterpene methyltransferase gene accumulated methylated squalene derivatives.

Figure 17:
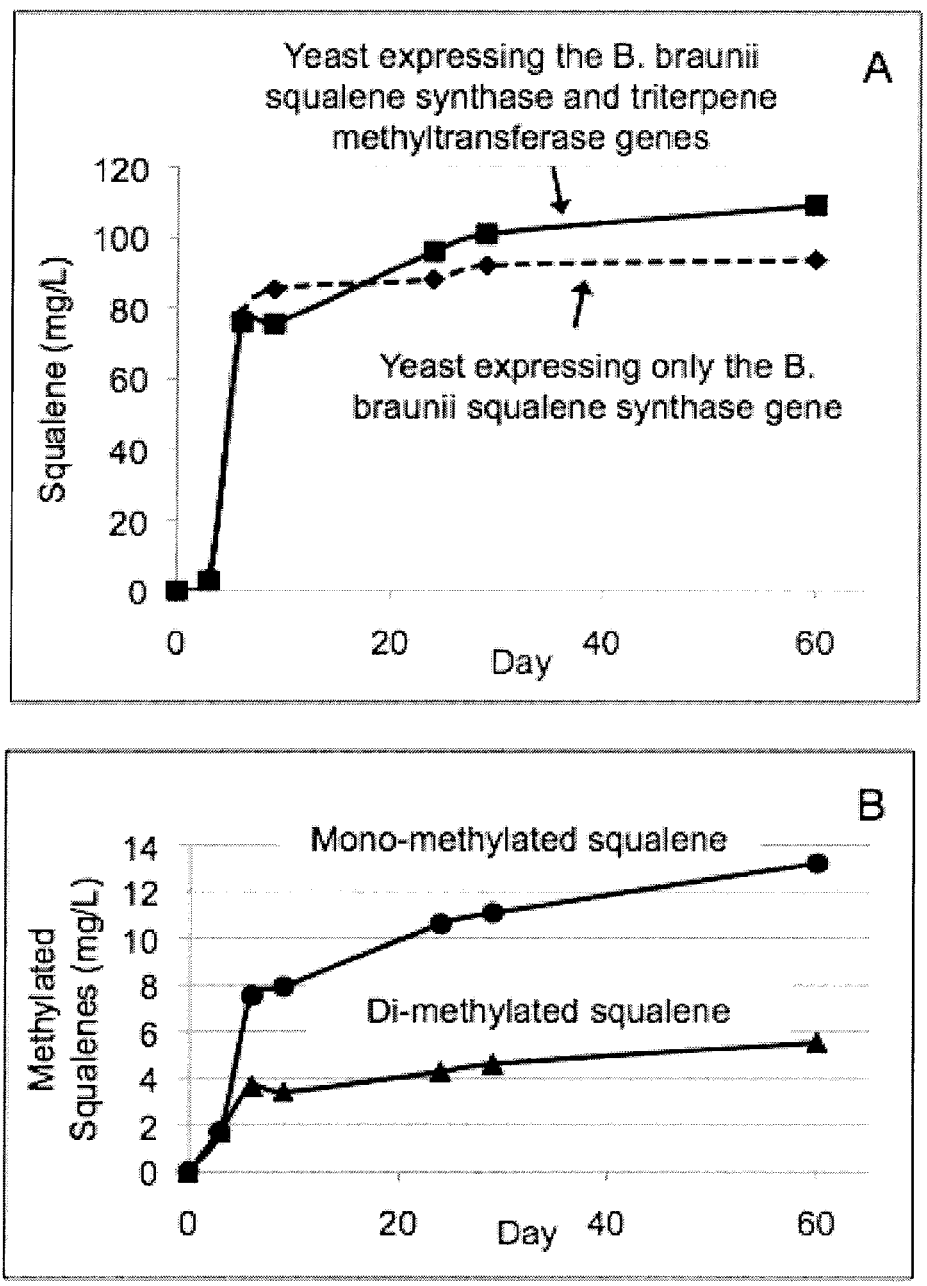
FIG. 17 depicts the accumulation of mono- and di-methylate squalene in a time dependent manner.

Yeast that were engineered to over-express the *B. braunii* squalene synthase gene, or both the *B. braunii* squalene synthase and triterpene methyltransferase genes accumulate squalene in the same time dependent fashion and to the same levels (FIG. 17, panel A). Only the yeast over-expressing both the squalene synthase and triterpene methyltransferase accumulated mono- and di-methylate squalene in a time dependent manner (FIG. 17, panel B). Growth of the yeast, and extraction and detection of squalene and squalene derivatives were as described in FIG. 14.

It will be appreciated that, although specific embodiments of the invention have been described herein for purposes of illustration, various modifications may be made without departing from the spirit and scope of the invention. All such modifications and variations are intended to be included herein within the scope of this disclosure and the present invention and protected by the following claims.

We claim:

1. An isolated cDNA which encodes a polypeptide which comprises the amino acid sequence of SEQ ID NO:2.

2. A recombinant vector comprising an isolated nucleic acid which encodes a polypeptide which comprises the amino acid sequence of SEQ ID NO: 2.

3. The vector of claim 2 which is an expression vector.

4. A host cell transfected with the vector of claim 2.

5. The host cell of claim 4 wherein the cell is prokaryotic or eukaryotic.

6. The host cell of claim 5 wherein the prokaryotic cell is a bacterial cell and the wherein the eukaryotic cell is a fungal cell, plant cell or animal cell.

7. The host cell of claim 6, where in the plant cell is a transfected terrestrial plant cell or a transfected algae cell.

8. The host cell of claim 4 further transfected with a nucleic acid molecule that encodes a farnesyl diphosphate synthase and/or a nucleic acid molecule that encodes a triterpene synthase.

9. The host cell of claim 8 wherein the triterpene synthase is a squalene synthase or a botryococcene synthase.

10. The host cell of claim 4 further transfected with a nucleic acid molecule that encodes a farnesyl diphosphate synthase and a nucleic acid molecule that encodes a triterpene synthase, and wherein the triterpene methyltransferase, farnesyl diphosphate synthase and triterpene synthase are all expressed in the cytoplasm or are all expressed in the in a chloroplast.

11. A method of producing a methylated triterpene, the method comprising providing a metabolizable of carbon source to a host cell transfected with a nucleic acid molecule that encodes a triterpene methyltransferase under conditions sufficient for production of a methylated triterpene wherein the nucleic acid molecule comprises SEQ ID NO: 1.

12. An isolated polypeptide having triterpene methyltransferase activity comprising SAM (S-adenosyl methionine) and SMT (sterol methyltransferase specific) binding motifs wherein the SAM and SMT binding motifs are (a) SMT-1 wherein the amino acid sequence of SMT-1 is SEQ ID NO: 14, (b) SAM-I wherein the amino acid sequence of SAM-I is SEQ ID NO: 15, (c) SAM-II wherein the amino acid sequence of SAM-II is SEQ ID NO: 16, (d) SMT-II wherein the amino acid sequence of SMT-II is SEQ ID NO: 17 and (e) SAM-III wherein the amino acid sequence of SAM-III is SEQ ID NO: 18.

13. The isolated polypeptide of claim 12 wherein the polypeptide comprises SEQ ID NO: 2.

14. A method of producing a methylated triterpene, the method comprising providing a metabolizable of carbon source to a host cell transfected with a nucleic acid molecule that encodes a triterpene methyltransferase of claim 12 under conditions sufficient for production of a methylated triterpene.

15. The method of claim 14 further comprising isolating the methylated triterpene produced by the host cell.

16. The method of claim 14 wherein the methylated triterpene comprises methylated botryococcenes and/or methylated squalenes.

17. The method of claim 14 wherein the host cell is a prokaryotic cell or a eukaryotic cell.

18. The method of claim 17 wherein the prokaryotic host cell is a bacterial cell and the eukaryotic host cell is a fungal cell, plant cell or animal cell.

19. The method of claim 18 wherein the plant cell is a transfected terrestrial plant cell or a transfected algae.

20. The method of claim 14 wherein the host cell is further transfected with a nucleic acid molecule that encodes a farnesyl diphosphate synthase and/or a nucleic acid molecule that encodes a triterpene synthase.

21. The method of claim 20 wherein the triterpene synthase is a squalene synthase or a botryococcene synthase.

22. The method claim 19 wherein the terrestrial plant cell is further transfected with a nucleic acid molecule that encodes a farnesyl diphosphate synthase and a nucleic acid molecule that encodes a triterpene synthase, and wherein the nucleic acids encoding triterpene methyltransferase, farnesyl diphosphate synthase and triterpene synthase are all targeted for expression in a chloroplast.

* * * * *

SEQUENCE LISTING

<160> NUMBER OF SEQ ID NOS: 45

<210> SEQ ID NO 1
<211> LENGTH: 1140
<212> TYPE: DNA
<213> ORGANISM: B. braunii

<400> SEQUENCE: 1

```
atggccctgg atcttctttc atcctacgct cctggcttgg tcgaaagcct gctaacatgg      60
aaaggcgcag ccggcttggc tgcagctgtt gccctgggct atattattat aagcaacctt     120
cctggaaggc aggttgctaa gcccagcctt cttcaagtca gaactggtgg cgtcgccttc     180
gagaaggtcg ctgaggtagt tgccgactac agtgactctt acgggcaaac tgaaaagggc     240
gaactcatcg tcaaggacaa caacaagatt gtctctctcg cgaatacttt ctatgacctc     300
atcaccgatg gatatgagtg gggatggggc tccggcttcc acttctctca taggctgcca     360
gggatgtcct tcaatgcatc tcagctgctc catgagtccc gtatggcgtc tttcctgcgc     420
ctgaagcccg gcatgcaagt tcttgatgtt ggctgcggtg tcggaaaccc tggcagaacg     480
gttgctgcct gcagtggagc agtggtgact ggcatcacca tcaatgcata ccagatcaag     540
cgcgctgagt tgcacactaa gcgggcgggc ttggtaggat acttcaagcc agttcaggga     600
aacttctgcg cgatgccttt ccaagacaag agcttcgatg ctgcctttgc catggactct     660
acttgccatg cccccaagct ggaggatgtg tactccgagg tcttccgcgt gttgaagcct     720
ggcgcatact ttgcaactta tgagtgggtg tctacaaaga actacgactc caacaaccca     780
gagcacgtga agtgcatgaa cagcatcatc ctgggcaatg cctgccgaa catcaggagt     840 tggaagcaag ctgaggaggc agggaagaac gtgggtttca acctgcttac cagcctcgac     900
atggctacaa actcccccat cggaaagccc tggtactctg tcccagagcg catggtaaac     960
tggggcctgt ccgtttcca caaggcttgc attcgcactg cctctaccct gcatctgctg    1020
ccgccagaat cctggaagtt cttctacatc cttgcagaga tggccgagaa ccttgtaaag    1080
ggtgggcaat gggacatctt cacccccatg cacttgctga tcttccaaaa gccagagtaa    1140
```

<210> SEQ ID NO 2
<211> LENGTH: 379
<212> TYPE: PRT
<213> ORGANISM: B.Braunii

<400> SEQUENCE: 2

```
Met Ala Leu Asp Leu Leu Ser Ser Tyr Ala Pro Gly Leu Val Glu Ser
1               5                   10                  15

Leu Leu Thr Trp Lys Gly Ala Ala Gly Leu Ala Ala Ala Val Ala Leu
            20                  25                  30

Gly Tyr Ile Ile Ile Ser Asn Leu Pro Gly Arg Gln Val Ala Lys Pro
        35                  40                  45

Ser Leu Leu Gln Val Arg Thr Gly Gly Val Ala Phe Glu Lys Val Ala
    50                  55                  60

Glu Val Val Ala Asp Tyr Ser Asp Ser Tyr Gly Gln Thr Glu Lys Gly
65                  70                  75                  80

Glu Leu Ile Val Lys Asp Asn Asn Lys Ile Val Ser Leu Ala Asn Thr
                85                  90                  95

Phe Tyr Asp Leu Ile Thr Asp Gly Tyr Glu Trp Gly Trp Gly Ser Gly
            100                 105                 110

Phe His Phe Ser His Arg Leu Pro Gly Met Ser Phe Asn Ala Ser Gln
        115                 120                 125

Leu Leu His Glu Ser Arg Met Ala Ser Phe Leu Arg Leu Lys Pro Gly
    130                 135                 140

Met Gln Val Leu Asp Val Gly Cys Gly Val Gly Asn Pro Gly Arg Thr
145                 150                 155                 160

Val Ala Ala Cys Ser Gly Ala Val Val Thr Gly Ile Thr Ile Asn Ala
                165                 170                 175
```

-continued

```
Tyr Gln Ile Lys Arg Ala Glu Leu His Thr Lys Arg Ala Gly Leu Val
            180                 185                 190
Gly Tyr Phe Lys Pro Val Gln Gly Asn Phe Cys Ala Met Pro Phe Gln
        195                 200                 205
Asp Lys Ser Phe Asp Ala Ala Phe Ala Met Asp Ser Thr Cys His Ala
    210                 215                 220
Pro Lys Leu Glu Asp Val Tyr Ser Glu Val Phe Arg Val Leu Lys Pro
225                 230                 235                 240
Gly Ala Tyr Phe Ala Thr Tyr Glu Trp Val Ser Thr Lys Asn Tyr Asp
                245                 250                 255
Ser Asn Asn Pro Glu His Val Lys Cys Met Asn Ser Ile Ile Leu Gly
            260                 265                 270
Asn Gly Leu Pro Asn Ile Arg Ser Trp Lys Gln Ala Glu Glu Ala Gly
        275                 280                 285
Lys Asn Val Gly Phe Asn Leu Leu Thr Ser Leu Asp Met Ala Thr Asn
    290                 295                 300
Ser Pro Ile Gly Lys Pro Trp Tyr Ser Val Pro Glu Arg Met Val Asn
305                 310                 315                 320
Trp Gly Leu Phe Arg Phe His Lys Ala Cys Ile Arg Thr Ala Ser Thr
                325                 330                 335
Leu His Leu Leu Pro Pro Glu Ser Trp Lys Phe Phe Tyr Ile Leu Ala
            340                 345                 350
Glu Met Ala Glu Asn Leu Val Lys Gly Gly Gln Trp Asp Ile Phe Thr
        355                 360                 365
Pro Met His Leu Leu Ile Phe Gln Lys Pro Glu
    370                 375

<210> SEQ ID NO 3
<211> LENGTH: 32
<212> TYPE: DNA
<213> ORGANISM: Artificial Sequence
<220> FEATURE:
<223> OTHER INFORMATION: TMT cDNA forward primer

<400> SEQUENCE: 3
cggaattcat ggccctggat cttctttcat cc                                    32

<210> SEQ ID NO 4
<211> LENGTH: 34
<212> TYPE: DNA
<213> ORGANISM: Artificial Sequence
<220> FEATURE:
<223> OTHER INFORMATION: TMT cDNA reverse primer

<400> SEQUENCE: 4
ggggaagctt ttactctggc ttttggaaga tcag                                  34

<210> SEQ ID NO 5
<211> LENGTH: 34
<212> TYPE: DNA
<213> ORGANISM: Artificial Sequence
<220> FEATURE:
<223> OTHER INFORMATION: TMT cDNA reverse primer

<400> SEQUENCE: 5
ggggaagctt ttactctggc ttttggaaga tcag                                  34

<210> SEQ ID NO 6
<211> LENGTH: 45
<212> TYPE: DNA
<213> ORGANISM: Artificial Sequence
```

```
<220> FEATURE:
<223> OTHER INFORMATION: TMT cDNA forward pirmer

<400> SEQUENCE: 6
ttggcgcgcc agccctggat cttctttcat cctacgctcc tggct            45

<210> SEQ ID NO 7
<211> LENGTH: 46
<212> TYPE: DNA
<213> ORGANISM: Artificial Sequence
<220> FEATURE:
<223> OTHER INFORMATION: Reverse primer

<400> SEQUENCE: 7
ggggcggccg cttactctgg cttttggaag atcagcaagt gcatgg           46

<210> SEQ ID NO 8
<211> LENGTH: 57
<212> TYPE: DNA
<213> ORGANISM: Artificial Sequence
<220> FEATURE:
<223> OTHER INFORMATION: Reverse primer

<400> SEQUENCE: 8
ggggaccact ttgtacaaga aagctgggtt taggcgctga gtgagtgtgg gtctagg    57

<210> SEQ ID NO 9
<211> LENGTH: 57
<212> TYPE: DNA
<213> ORGANISM: Artificial Sequence
<220> FEATURE:
<223> OTHER INFORMATION: Forward primer

<400> SEQUENCE: 9
ggggacaagt ttgtacaaaa aagcaggcta aaagaatggg gatgcttcgc tggggag    57

<210> SEQ ID NO 10
<211> LENGTH: 23
<212> TYPE: DNA
<213> ORGANISM: Artificial Sequence
<220> FEATURE:
<223> OTHER INFORMATION: Forward primer

<400> SEQUENCE: 10
atgtctgctg ttaacgttgc acc                                    23

<210> SEQ ID NO 11
<211> LENGTH: 22
<212> TYPE: DNA
<213> ORGANISM: Artificial Sequence
<220> FEATURE:
<223> OTHER INFORMATION: Reverse primer

<400> SEQUENCE: 11
ttaaccaatc aactcaccaa ac                                     22

<210> SEQ ID NO 12
<211> LENGTH: 20
<212> TYPE: DNA
<213> ORGANISM: Artificial Sequence
<220> FEATURE:
<223> OTHER INFORMATION: Forward primer

<400> SEQUENCE: 12
acctctgaca catgcagctc                                        20
```

```
<210> SEQ ID NO 13
<211> LENGTH: 20
<212> TYPE: DNA
<213> ORGANISM: Artificial Sequence
<220> FEATURE:
<223> OTHER INFORMATION: Reverse primer

<400> SEQUENCE: 13
gcggtatttt ctccttacgc                                              20

<210> SEQ ID NO 14
<211> LENGTH: 12
<212> TYPE: PRT
<213> ORGANISM: B.Braunii

<400> SEQUENCE: 14

Gly Tyr Glu Trp Gly Trp Gly Ser Gly Phe His Phe
1               5                   10

<210> SEQ ID NO 15
<211> LENGTH: 11
<212> TYPE: PRT
<213> ORGANISM: B.Braunii

<400> SEQUENCE: 15

Val Leu Asp Val Gly Cys Gly Val Gly Asn Pro
1               5                   10

<210> SEQ ID NO 16
<211> LENGTH: 8
<212> TYPE: PRT
<213> ORGANISM: B. Braunii

<400> SEQUENCE: 16

Lys Ser Phe Asp Ala Ala Phe Ala
1               5

<210> SEQ ID NO 17
<211> LENGTH: 8
<212> TYPE: PRT
<213> ORGANISM: B.Braunii

<400> SEQUENCE: 17

Met Asp Ser Thr Cys His Ala Pro
1               5

<210> SEQ ID NO 18
<211> LENGTH: 9
<212> TYPE: PRT
<213> ORGANISM: B.Braunii

<400> SEQUENCE: 18

Val Leu Lys Pro Gly Ala Tyr Phe Ala
1               5

<210> SEQ ID NO 19
<211> LENGTH: 13
<212> TYPE: PRT
<213> ORGANISM: N. tabacum

<400> SEQUENCE: 19

Ile Tyr Glu Trp Gly Trp Gly Gln Ser Phe His Phe Ser
1               5                   10

<210> SEQ ID NO 20
<211> LENGTH: 11
```

-continued

```
<212> TYPE: PRT
<213> ORGANISM: N. tabacum

<400> SEQUENCE: 20

Ile Leu Asp Ala Gly Cys Gly Val Gly Pro
1               5                   10

<210> SEQ ID NO 21
<211> LENGTH: 8
<212> TYPE: PRT
<213> ORGANISM: N. tabacum

<400> SEQUENCE: 21

Asn Ser Phe Asp Gly Ala Tyr Ser
1               5

<210> SEQ ID NO 22
<211> LENGTH: 8
<212> TYPE: PRT
<213> ORGANISM: N. tabacum

<400> SEQUENCE: 22

Ile Glu Ala Thr Cys His Ala Pro
1               5

<210> SEQ ID NO 23
<211> LENGTH: 9
<212> TYPE: PRT
<213> ORGANISM: N. tabacum

<400> SEQUENCE: 23

Val Met Lys Pro Gly Ser Leu Tyr Val
1               5

<210> SEQ ID NO 24
<211> LENGTH: 12
<212> TYPE: PRT
<213> ORGANISM: A. thaliana

<400> SEQUENCE: 24

Ile Tyr Glu Trp Gly Trp Gly Gln Ser Phe His Phe
1               5                   10

<210> SEQ ID NO 25
<211> LENGTH: 11
<212> TYPE: PRT
<213> ORGANISM: A. thaliana

<400> SEQUENCE: 25

Val Leu Asp Val Gly Cys Gly Ile Gly Gly Pro
1               5                   10

<210> SEQ ID NO 26
<211> LENGTH: 8
<212> TYPE: PRT
<213> ORGANISM: A. thaliana

<400> SEQUENCE: 26

Asn Ser Phe Asp Ala Val Tyr Ala
1               5

<210> SEQ ID NO 27
<211> LENGTH: 8
<212> TYPE: PRT
<213> ORGANISM: A. thaliana
```

```
<400> SEQUENCE: 27

Ile Glu Ala Thr Cys His Ala Pro
1               5

<210> SEQ ID NO 28
<211> LENGTH: 9
<212> TYPE: PRT
<213> ORGANISM: A. thaliana

<400> SEQUENCE: 28

Val Leu Lys Pro Gly Gln Cys Phe Ala
1               5

<210> SEQ ID NO 29
<211> LENGTH: 13
<212> TYPE: PRT
<213> ORGANISM: Z. mays

<400> SEQUENCE: 29

Phe Tyr Glu Tyr Gly Trp Gly Glu Ser Phe His Phe Ala
1               5                   10

<210> SEQ ID NO 30
<211> LENGTH: 11
<212> TYPE: PRT
<213> ORGANISM: Z. mays

<400> SEQUENCE: 30

Val Leu Asp Val Gly Cys Gly Ile Gly Gly Pro
1               5                   10

<210> SEQ ID NO 31
<211> LENGTH: 8
<212> TYPE: PRT
<213> ORGANISM: Z. mays

<400> SEQUENCE: 31

Asn Thr Phe Asp Ala Val Tyr Ala
1               5

<210> SEQ ID NO 32
<211> LENGTH: 8
<212> TYPE: PRT
<213> ORGANISM: Z. mays

<400> SEQUENCE: 32

Ile Glu Ala Thr Cys His Ala Pro
1               5

<210> SEQ ID NO 33
<211> LENGTH: 9
<212> TYPE: PRT
<213> ORGANISM: Z.mays

<400> SEQUENCE: 33

Val Leu Lys Pro Gly Gln Cys Phe Ala
1               5

<210> SEQ ID NO 34
<211> LENGTH: 13
<212> TYPE: PRT
<213> ORGANISM: O. sativa

<400> SEQUENCE: 34

Ile Tyr Glu Trp Gly Trp Gly Gln Ser Phe His Phe Ser
```

```
1               5                   10
```

<210> SEQ ID NO 35
<211> LENGTH: 11
<212> TYPE: PRT
<213> ORGANISM: O. sativa

<400> SEQUENCE: 35

```
Leu Leu Asp Val Gly Cys Gly Val Gly Pro
1               5                   10
```

<210> SEQ ID NO 36
<211> LENGTH: 8
<212> TYPE: PRT
<213> ORGANISM: O. sativa

<400> SEQUENCE: 36

```
Asn Ser Phe Asp Gly Ala Tyr Ser
1               5
```

<210> SEQ ID NO 37
<211> LENGTH: 8
<212> TYPE: PRT
<213> ORGANISM: O. sativa

<400> SEQUENCE: 37

```
Ile Glu Ala Thr Cys His Ala Pro
1               5
```

<210> SEQ ID NO 38
<211> LENGTH: 9
<212> TYPE: PRT
<213> ORGANISM: O. sativa

<400> SEQUENCE: 38

```
Val Leu Lys Pro Gly Gly Leu Tyr Val
1               5
```

<210> SEQ ID NO 39
<211> LENGTH: 13
<212> TYPE: PRT
<213> ORGANISM: S. cerevisiae

<400> SEQUENCE: 39

```
Phe Tyr Glu Tyr Gly Trp Gly Ser Ser Phe His Phe Ser
1               5                   10
```

<210> SEQ ID NO 40
<211> LENGTH: 11
<212> TYPE: PRT
<213> ORGANISM: S. cerevisiae

<400> SEQUENCE: 40

```
Val Leu Asp Val Gly Cys Gly Val Gly Pro
1               5                   10
```

<210> SEQ ID NO 41
<211> LENGTH: 8
<212> TYPE: PRT
<213> ORGANISM: S. cerevisiae

<400> SEQUENCE: 41

```
Asn Thr Phe Asp Lys Val Tyr Ala
1               5
```

```
<210> SEQ ID NO 42
<211> LENGTH: 8
<212> TYPE: PRT
<213> ORGANISM: S. cerevisiae

<400> SEQUENCE: 42

Ile Glu Ala Thr Cys His Ala Pro
1               5

<210> SEQ ID NO 43
<211> LENGTH: 9
<212> TYPE: PRT
<213> ORGANISM: S. cerevisiae

<400> SEQUENCE: 43

Val Leu Lys Pro Gly Gly Thr Phe Ala
1               5

<210> SEQ ID NO 44
<211> LENGTH: 186
<212> TYPE: DNA
<213> ORGANISM: Artificial sequence
<220> FEATURE:
<223> OTHER INFORMATION: Chloroplast targeting sequence

<400> SEQUENCE: 44
atggcttcct ctatgctctc ctccgccgct gtggttacat ccccggctca ggccaccatg      60
gtcgctccat tcaccggctt gaagtcatcc gctgcattcc cggtcacccg caagaccaac     120
aaggacatca cttccatcgc aagcaacggg ggaagatcta gctgcatgaa ggagctcggc     180
gcgcct                                                                186

<210> SEQ ID NO 45
<211> LENGTH: 62
<212> TYPE: PRT
<213> ORGANISM: Artificial Sequence
<220> FEATURE:
<223> OTHER INFORMATION: Chloroplast targeting sequence

<400> SEQUENCE: 45

Met Ala Ser Ser Met Leu Ser Ser Ala Ala Val Val Thr Ser Pro Ala
1               5                   10                  15

Gln Ala Thr Met Val Ala Pro Phe Thr Gly Leu Lys Ser Ser Ala Ala
            20                  25                  30

Phe Pro Val Thr Arg Lys Thr Asn Lys Asp Ile Thr Ser Ile Ala Ser
        35                  40                  45

Asn Gly Gly Arg Ser Ser Cys Met Lys Glu Leu Gly Ala Pro
    50                  55                  60
```